United States Patent
Osborne

(10) Patent No.: US 12,016,848 B2
(45) Date of Patent: *Jun. 25, 2024

(54) ROFLUMILAST FORMULATIONS WITH AN IMPROVED PHARMACOKINETIC PROFILE

(71) Applicant: Arcutis Biotherapeutics, Inc .., Westlake Village, CA (US)

(72) Inventor: David Osborne, Fort Collins, CO (US)

(73) Assignee: Arcutis Biotherapeutics, Inc., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,674

(22) Filed: Aug. 22, 2023

(65) Prior Publication Data

US 2024/0000760 A1     Jan. 4, 2024

Related U.S. Application Data

(60) Continuation of application No. 17/155,679, filed on Feb. 5, 2021, which is a continuation-in-part of application No. 17/102,056, filed on Nov. 23, 2020, now Pat. No. 11,793,796, which is a continuation of application No. 16/136,804, filed on Sep. 20, 2018, now Pat. No. 10,940,142, which is a continuation of application No. 15/848,505, filed on Dec. 20, 2017, now Pat. No. 10,105,354, which is a continuation of application No. 15/676,356, filed on Aug. 14, 2017, now Pat. No. 9,884,050, which is a division of application No. 15/616,409, filed on Jun. 7, 2017, now Pat. No. 9,895,359.

(51) Int. Cl.
*A61K 31/44*     (2006.01)
*A61K 9/00*      (2006.01)
*A61K 9/06*      (2006.01)
*A61K 9/14*      (2006.01)
*A61K 45/06*     (2006.01)
*A61K 47/10*     (2017.01)
*C09K 15/06*     (2006.01)

(52) U.S. Cl.
CPC ............ *A61K 31/44* (2013.01); *A61K 9/0014* (2013.01); *A61K 9/06* (2013.01); *A61K 9/145* (2013.01); *A61K 45/06* (2013.01); *A61K 47/10* (2013.01); *C09K 15/06* (2013.01)

(58) Field of Classification Search
CPC ......... A61K 31/44; A61K 47/10; C09K 15/06
See application file for complete search history.

(56) References Cited

U.S. PATENT DOCUMENTS

| | | |
|---|---|---|
| 4,482,537 A | 11/1984 | El-Menshawy et al. |
| 5,374,661 A | 12/1994 | Betlach, II |
| 5,712,298 A | 1/1998 | Amschler |
| 5,863,560 A | 1/1999 | Osborne |
| 6,056,955 A | 5/2000 | Fischetti et al. |
| 6,060,085 A | 5/2000 | Osborne |
| 6,106,848 A | 8/2000 | Preuilh et al. |
| 6,117,915 A | 9/2000 | Pereira et al. |
| 6,214,322 B1 | 4/2001 | Castro et al. |
| 7,470,791 B2 | 12/2008 | Kohl et al. |
| 7,951,398 B2 | 5/2011 | Dietrich et al. |
| 8,293,288 B2 | 10/2012 | Ma |
| 8,338,648 B2 | 12/2012 | Stock et al. |
| 8,377,663 B2 | 2/2013 | Lintner et al. |
| 8,536,206 B2 | 9/2013 | Kohl et al. |
| 8,618,142 B2 | 12/2013 | Kohl et al. |
| 8,884,034 B2 | 11/2014 | Daynard et al. |
| 9,205,044 B2 | 12/2015 | Linder |
| 9,649,302 B2 | 5/2017 | Vakkalanka |
| 9,884,050 B1 | 2/2018 | Osborne |
| 9,895,359 B1 | 2/2018 | Osborne |
| 9,907,788 B1 | 3/2018 | Osborne |
| 10,105,354 B1 | 10/2018 | Osborne |

(Continued)

FOREIGN PATENT DOCUMENTS

| | | |
|---|---|---|
| CN | 1655782 | 8/2005 |
| CN | 101061993 A | 10/2007 |

(Continued)

OTHER PUBLICATIONS

DALIRESP trademark registration certificate No. 4,003,351. (Year: 2011).*
Akhtar et al., "Exploring preclinical and clinical effectiveness of nanoformulations in the treatment of atopic dermatitis: Safety aspects and patent reviews," Bulletin of Faculty of Pharmacy, Cairo University 55 (2017), 1-10.
Bardin P et al. "Roflumilast for asthma: Efficacy findings in mechanism of action studies." Pulmonary Pharmacology & Therapeutics, vol. 35, Aug. 19, 2015, S4-S10.
Brown, "Treating COPD with PDE 4 inhibitors", International Journal of COPD 2007: 2(4) 517-533.
Examination Report cited in India Application No. 20194705011 dated Jul. 9, 2021. 6 pages.

(Continued)

*Primary Examiner* — Theodore R. Howell
(74) *Attorney, Agent, or Firm* — ROTHWELL, FIGG, ERNST & MANBECK, P.C.

(57) ABSTRACT

An improved a method of treating a patient having a disorder responsive to PDE-4 inhibition by administering roflumilast. The improvement involves administering the roflumilast topically in a composition having a roflumilast release profile that produces in the patient a flattened plasma concentration time curve and a reduced Cmax relative to oral administration of a PDE4-inhibiting amount of roflumilast. Such disorders include inflammatory disorders such as inflammatory dermatoses, including psoriasis, atopic dermatitis and seborrheic dermatitis. Such disorders also include inflammatory diseases in a variety of organs, especially the lungs (asthma, COPD). Because of reduced side effects with topical administration due to the improved pharmacokinetics (PK) characteristics, it may be possible to provide higher systemic exposures (AUCs) with topical administration, resulting in greater therapeutic efficacy than with the oral route of administration.

12 Claims, 24 Drawing Sheets

(56) References Cited

U.S. PATENT DOCUMENTS

| | | | |
|---|---|---|---|
| 10,172,841 | B2 | 1/2019 | Osborne |
| 10,940,142 | B2 | 3/2021 | Osborne |
| 11,129,818 | B2 | 9/2021 | Osborne et al. |
| 11,534,493 | B2 * | 12/2022 | Osborne ............. A61K 9/0014 |
| 11,707,454 | B2 | 7/2023 | Bolle et al. |
| 11,793,796 | B2 * | 10/2023 | Osborne ............... A61K 45/06 |
| 11,819,496 | B2 | 11/2023 | Osborne |
| 2005/0112162 | A1 | 5/2005 | Drader |
| 2005/0244339 | A1 | 11/2005 | Jauernig et al. |
| 2006/0084684 | A1 | 4/2006 | Bolle |
| 2006/0110415 | A1 * | 5/2006 | Gupta .................. A61K 8/0212 424/59 |
| 2006/0153905 | A1 | 7/2006 | Carrara |
| 2006/0204452 | A1 | 9/2006 | Lathrop et al. |
| 2006/0204526 | A1 | 9/2006 | Lathrop |
| 2006/0234006 | A1 | 10/2006 | Terra |
| 2007/0048241 | A1 | 3/2007 | Obukowho et al. |
| 2007/0098660 | A1 | 5/2007 | Taneri et al. |
| 2007/0207107 | A1 | 9/2007 | Winckle et al. |
| 2007/0258935 | A1 | 11/2007 | McEntire et al. |
| 2007/0259009 | A1 | 11/2007 | Linder |
| 2007/0287689 | A1 | 12/2007 | Harada |
| 2008/0200005 | A1 | 1/2008 | Chang et al. |
| 2008/0039405 | A1 | 2/2008 | Langley |
| 2008/0045572 | A1 | 2/2008 | Linder |
| 2008/0280958 | A1 | 11/2008 | Bolle et al. |
| 2009/0104132 | A1 | 4/2009 | Segura-Orsoni |
| 2009/0214628 | A1 | 8/2009 | De Rijk |
| 2009/0220583 | A1 | 9/2009 | Pereswetoff-Morath et al. |
| 2011/0117182 | A1 | 5/2011 | Ahluwalia et al. |
| 2011/0212157 | A1 | 9/2011 | Edelson et al. |
| 2012/0252793 | A1 | 10/2012 | Bream et al. |
| 2013/0005816 | A1 | 1/2013 | Chen |
| 2013/0017282 | A1 | 1/2013 | Ma |
| 2013/0018104 | A1 | 1/2013 | Lathrop et al. |
| 2013/0217742 | A1 | 8/2013 | Yang |
| 2014/0112991 | A1 | 4/2014 | Johnson et al. |
| 2014/0275184 | A1 | 9/2014 | Jones et al. |
| 2014/0275265 | A1 | 9/2014 | Mattison |
| 2014/0296191 | A1 | 10/2014 | Patel et al. |
| 2014/0303215 | A1 | 10/2014 | Bolle et al. |
| 2015/0099752 | A9 | 4/2015 | Bernal Anchuela et al. |
| 2015/0297601 | A1 | 10/2015 | Henkin |
| 2016/0030435 | A1 | 2/2016 | Henkin |
| 2017/0152273 | A1 | 6/2017 | Merchant |
| 2017/0266289 | A1 | 9/2017 | Lipari |
| 2018/0353490 | A1 | 12/2018 | Osborne |
| 2019/0091333 | A1 | 3/2019 | Osborne |
| 2019/0175491 | A1 | 6/2019 | Abraham et al. |
| 2019/0365642 | A1 | 12/2019 | Osborne et al. |
| 2020/0155524 | A1 | 5/2020 | Welgus et al. |
| 2020/0163944 | A1 | 5/2020 | Osborne et al. |
| 2021/0161870 | A1 | 6/2021 | Welgus et al. |
| 2021/0275509 | A1 | 9/2021 | Welgus et al. |
| 2021/0386719 | A1 | 12/2021 | Osborne et al. |
| 2022/0211730 | A1 | 7/2022 | Osborne et al. |
| 2023/0091358 | A1 | 3/2023 | Osborne et al. |
| 2023/0201177 | A1 | 6/2023 | Osborne |
| 2023/0285319 | A1 | 9/2023 | Osborne et al. |
| 2023/0310345 | A1 | 10/2023 | Osborne et al. |

FOREIGN PATENT DOCUMENTS

| | | |
|---|---|---|
| CN | 101854907 | 10/2010 |
| CN | 112384199 | 2/2021 |
| EP | 1511516 | 3/2005 |
| JP | 2005529930 | 10/2005 |
| JP | 2007119432 A | 5/2007 |
| JP | 2007533606 | 11/2007 |
| JP | 2009034537 A2 | 3/2009 |
| JP | 2011219364 | 11/2011 |
| JP | 2012532871 A | 12/2012 |
| WO | 9501338 | 1/1995 |
| WO | 9810768 | 3/1998 |
| WO | 2003099334 | 12/2003 |
| WO | WO 2005/016296 A1 | 2/2005 |
| WO | 2005115322 | 12/2005 |
| WO | 2013030789 | 3/2013 |
| WO | 2013081565 | 6/2013 |
| WO | 2014055801 | 4/2014 |
| WO | 2014130922 | 8/2014 |
| WO | 2014201541 | 12/2014 |
| WO | 2015132708 | 9/2015 |
| WO | 2016033308 | 3/2016 |
| WO | 2017216738 | 12/2017 |
| WO | 2018144093 A2 | 8/2018 |
| WO | 2018226584 | 12/2018 |
| WO | 2019060379 | 3/2019 |
| WO | 2021045804 | 3/2021 |

OTHER PUBLICATIONS

Examination Report cited in India Application No. 202047016247 dated Jun. 28, 2021. 4 pages.
Final Office Action issued in U.S. Appl. No. 15/712,900 dated May 23, 2022. 14 pages.
Huang, J. et al., "Pharmacokinetics of single- and multiple-dose roflumilast: an open-label, three-way crossover study in healthy Chinese volunteers." Drug Design, Development and Therapy, 2018(12). pp. 4047-4057.
International Search Report and Written Opinion cited in PCT/US2018/051691 dated Nov. 22, 2018, 11 pages.
International Preliminary Report on Patentability and Written Opinion cited PCT/US2018/051691 dated Mar. 24, 2020. 6 pages.
International Preliminary Report on Patentability and Written Opinion cited in PCT/US2018/051691 dated Apr. 2, 2020. 8 pages.
International Search Report issued in PCT/US2021/031144 dated Sep. 21, 2021. 2 pages.
Ip.com translation KR1999-0015251 A, printed 2022 (year2022), 1 page.
Julian N. Mayba et al. Review of Atopic Dermatitis and Topical Therapies:, Journal of Cutaneous Medicine and Surgery, BC Decker Inc. CA. vol. 21 No. 3 Dec. 27, 2016, pp. 227-236.
Karande et al., "Enhancement of transdermal drug delivery via synergistic action of chemicals", Biochimica Et Biophysica Acta, 1788 (2009), pp. 2632-2373.
Kawamatawong, "Roles of roflumilast, a selective phosphodiesterase 4 inhibitor in airway diseases," J. Thorac Dis 2017. 9(4). 1144-1154.
Kircik, L et al., "Rational Vehicle Design Ensures Targeted Cutaneous Steroid Delivery." Journal of Clinical and Aesthetic Dermatology 10(2). Feb. 2017. pp. 12-19.
Lorimer, "Thermodynamics of solubility in mixed solvent systems", Pure & Appl. Chem., 1993, vol. 65, 2, pp. 183-191.
Minghetti et al., "Ex Vivo Study of Transdermal Permeation of Four Diclofenac Salts from Different Vehicles", Journal of Pharmaceutical Sciences, vol. 96, No. 4, Apr. 2007, pp. 814-823.
Nair et al., "Basic considerations in the dermatokinetics of topical formulations", Brazilian Journal of Pharmaceutical Sciences, vol. 43, No. 3, Jul./Sep. 2013, pp. 423-434.
Notification of Transmittal of the International Search Report and The Written Opinion of the International Searching Authority cited in PCT/US2020/29008 dated Jul. 6, 2020. 12 pages.
Notification of Transmittal of the International Search Report and Written Opinion cited in PCT/US2019/034640 dated Dec. 4, 2019, 10 pages.
Notification of Transmittal of the International Search Report and The Written Opinion of the International Searching Authority cited in PCT/US2021/015740 dated Apr. 23, 2021. 17 pages.
Notification of Transmittal of the International Search Report and Written Opinion of the International Searching Authority issued in PCT/US2022/013344 dated Jun. 9, 2022, 16 pages.
Notification of Transmittal of the International Search Report and the Written Opinion of the International Searching Authority issued in PCT/US2021/061871, dated Apr. 5, 2022. 12 pages.
Notification of Transmittal of the International Search Report and Written Opinion cited in PCT/US2019/034640, dated Dec. 4, 2019, 14 pages.

(56) References Cited

OTHER PUBLICATIONS

Office Action issued in MX/a/2019/014741 dated Nov. 4, 2022 (7 pages).
Osborne, "Diethylene glycol monoethyl ether: an emerging solvent in topical dermatology products", J. Cosmet Dermatol, Dec. 2011, 10(4), pp. 324-329.
Pathan et al., "Chemical Penetration Enhancers for Transdermal Drug Delivery Systems", Tropical Journal of Pharmaceutical Research, Apr. 2009, 8(2), pp. 173-179.
Patzelt et al., "Hair follicles, their disorders and their opportunities", Drug Discovery Today: Disease Mechanisms, vol. 5, Issue 2, Summer 2008, pp. e173-e-181.
PCT International Search Report and Written Opinion issued in PCT/US2018/0358584 on Aug. 17, 2018, 12 pages.
Pudipeddi et al., "Trends in Solubility of Polymorphs", Journal of Pharmaceutical Sciences, May 2005, vol. 94, Issue 5, pp. 929-939, Abstract only.
Shakeel et al. "Solubilization behavior of paracetamol in Transcutol—water mixtures at (298.15 to 333.15) K," Journal of Chemical & Engineering Data 58:3551-3556, 2013.
Sikarra et al., "Techniques for Solubility Enhancement of Poorly Soluble Drugs: An Overview", Journal of Medical Pharmaceutical and Allied Sciences, (2012), 01; pp. 1-22.
Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Special Chem "Ethoxydiglycol ," printed 2019; https://cosmetics.specialchem.com/inci/ethoxydiglycol.
TRADENAME (roflumilast) Tablets NDA 22-522, Summary of Basis for the Recommended Action from Chemistry, Manufacturing, and Controls, Forest Research Institute, Inc., Reference ID 2901509, Jul. 2009, 3 pages.
Translation Abstract. of Office Action for Chinese Patent Application No. 201810581282.7 dated Oct. 22, 2019; 13 pages.
Wikipedia "Corticosteroid," last edited Nov. 15, 2019; https://en.wikipedia.org/wiki/Corticosteroid.
Wittmann et al. "Phosphodiesterase 4 Inhibition in the Treatment of Psoriasis, Psoratic Arthritis and Other Chronic Inflammatory Diseases". Dermatol Ther(Heidelb) (2013) 3:1-15.
E P Bezuglaya et al., "Water-Hexylene Glycol System as A Potential Medicinal Base", Pharmaceutical Chemistry, vol. 47, pp. 281-286. 2013.
Pre-grant Opposition documents filed for Indian Application No. 201947050111, Apr. 5, 2023, 38 pages.
Osborne et al., "Skin Penetration and Permeation Properties of Transcutol®—Neat or Diluted Mixtures", AAPS PharmaSCITECH, vol. 19, No. 8, Nov. 2018, pp. 3512-3533.
Notification of Certification of Invalidity, Unenforceability, and/or Noninfringement for U.S. Pat. Nos. 9,884,050; 9,907,788; 10,940,142; 11,129,818; 11,793,796; and 11,819,496 Pursuant to § 505(j)(2)(B)(iv) of the Federal Food, Drug, & Cosmetic Act, Feb. 13, 2024.
U.S. Non-Final Office Action mailed Feb. 5, 2024 in corresponding U.S. Appl. No. 17/155,679, First Named Inventor: David W. Osborne (10 pages).
Sullivan DW Jr, Gad SC, Julien M. A review of the nonclinical safety of Transcutol(R), a highly purified form of diethylene glycol monoethyl ether (DEGEE) used as a pharmaceutical excipient. Food Chem Toxicol. 2014;72:40-50.
Helton DR, Osborne DW, Pierson SK, Buonarati MH, Bethem RA. Pharmacokinetic profiles in rats after intravenous, oral, or dermal administration of dapsone. Drug Metab Dispos. 2000;28(8):925-9.
Gad SC, Cassidy CD, Aubert N, Spainhour B, Robbe H. Nonclinical vehicle use in studies by multiple routes in multiple species. Int J Toxicol. 2006;25(6):499-521.
Chadha G, Sathigari S, Parsons DL, Jayachandra Babu R. In vitro percutaneous absorption of genistein from topical gels through human skin. Drug Dev Ind Pharm. 2011;37(5):498-505.

Ganem-Quintanar A, Lafforgue C, Falson-Rieg F, Buri P. Evaluation of the transepidermal permeation of diethylene glycol monoethyl ether and skin water loss. Int J Pharm. 1997;147(2):165-71.
Dugard PH, Walker M, Mawdsley SJ, Scott RC. Absorption of some glycol ethers through human skin in vitro. Environ Health Perspect. 1984;57:193-7.
Koprda V, Bohacik L, & Hadgraft J Permeation of a Pyridoindol structure substance from the Transcutol/water/azone cosolvent system. In 5th International conference: Perspectives in Percutaneous Penetration. 1997.
Ritschel WA, Hussain AS. In vitro skin penetration of griseofulvin in rat and human skin from an ointment dosage form. Arzneimittelforschung. 1988;38(11):1630-2.
Bialik W, Walkers KA, Brain KR, Hadgraft J. Some factors affecting the in vitro penetration of ibuprofen through human skin. Int J Pharm. 1993;92:219-23.
Yazdanian M, Chen E. The effect of diethylene glycol monoethyl ether as a vehicle for topical delivery of ivermectin. Vet Res Commun. 1995;19(4):309-19.
Bjorklund S, et al. The effects of polar excipients transcutol and dexpanthenol on molecular mobility, permeability, and electrical impedance of the skin barrier. J Colloid Interface Sci. 2016;479:207-20.
Benson HA. Transdermal drug delivery: penetration enhancement techniques. Curr Drug Deliv. 2005;2(1):23-33.
Gwak HS, Kim SU, Chun IK. Effect of vehicles and enhancers on thein vitro permeation of melatonin through hairless mouse skin. Arch Pharm Res. 2002;25(3):392-6.
Harrison JE, Watkinson AC, Green DM, Hadgraft J, Brain K. The relative effect of azone and Transcutol on permeant diffusivity and solubility in human stratum corneum. Pharm Res. 1996;13(4):542-6.
Otto A, Wiechers JW, Kelly CL, Hadgraft J, du Plessis J. Effect of penetration modifiers on the dermal and transdermal delivery of drugs and cosmetic active ingredients. Skin Pharmacol Physiol. 2008;21(6):326-34.
Bonina FP, Montenegro L. Effects of some non-toxic penetration enhancers on in vitro heparin skin permeation from gel vehicles. Int J Pharm. 1994;111(2):191-6.
Puglia C, Bonina F, Trapani G, Franco M, Ricci M. Evaluation of in vitro percutaneous absorption of lorazepam and clonazepam from hydro-alcoholic gel formulations. Int J Pharm.2001;228(1-2):79-87.
Godwin DA, Kim NH, Felton LA. Influence of Transcutol CG on the skin accumulation and transdermal permeation of ultraviolet absorbers. Eur J Pharm Biopharm. 2002;53(1):23-7.
Ritschel WA, Panchagnula R, Stemmer K, Ashraf M. Development of an intracutaneous depot for drugs. Binding, drug accumulation and retention studies, and mechanism of depot. Skin Pharmacol. 1991;4(4):235-45.
Remane Y, Leopold CS, Maibach HI. Percutaneous penetration of methyl nicotinate from ointments using the laser Doppler technique: bioequivalence and enhancer effects. J Pharmacokinet Pharmacodyn. 2006;33(6):719-35.
Panchagnula R, Ritschel WA. Development and evaluation of an intracutaneous depot formulation of corticosteroids using Transcutol as a cosolvent: in-vitro, ex-vivo and in-vivo rat studies. J Pharm Pharmacol. 1991;43(9):609-14.
Cho YA, Gwak HS. Transdermal delivery of ketorolac tromethamine: effects of vehicles and penetration enhancers. Drug Dev Ind Pharm. 2004;30(6):557-64.
Salimi A, Hedayatipour N, Moghimipour E. The effect of various vehicles on the naproxen permeability through rat skin: a mechanistic study by DSC and FT-IR techniques. Adv Pharm Bull. 2016;6(1):9-16.
Moghadam SH, Saliaj E, Wettig SD, Dong C, Ivanova MV, Huzil JT, et al. Effect of chemical permeation enhancers on stratum corneum barrier lipid organizational structure and interferon alpha permeability. Mol Pharm. 2013;10(6):2248-60.
Watkinson AC, Hadgraft J, Bye A. Aspects of the transdermal delivery of prostaglandins. Int J Pharm. 1991;74(2-3):229-36.
Gwak H, Chun I. Effect of vehicles and penetration enhancers on the in vitro percutaneous absorption of tenoxicam through hairless mouse skin. Int J Pharm. 2002;236(1-2):57-64.

(56) References Cited

OTHER PUBLICATIONS

Gwak HS, Oh IS, Chun IK. Transdermal delivery of ondansetron hydrochloride: effects of vehicles and penetration enhancers. Drug Dev Ind Pharm. 2004;30(2):187-94.
Chang RK, Raw A, Lionberger R, Yu L. Generic development of topical dermatologic products: formulation development, process development, and testing of topical dermatologic products. AAPS J. 2013;15(1):41-52.
Choi JS, Cho YA, Chun IK, Jung SY, Gwak HS. Formulation and evaluation of ketorolac transdermal systems. Drug Deliv. 2007;14(2):69-74.
Hirata K, Helal F, Hadgraft J, Lane ME. Formulation of carbenoxolone for delivery to the skin. Int J Pharm. 2013;448(2):360-5.
Hirata K, Mohammed D, Hadgraft J, Lane ME. Influence of lidocaine hydrochloride and penetration enhancers on the barrier function of human skin. Int J Pharm. 2014;477(1-2):416-20.
Mura P, Faucci MT, Bramanti G, Corti P. Evaluation of transcutol as a clonazepam transdermal permeation enhancer from hydrophilic gel formulations. Eur J Pharm Sci. 2000;9(4):365-72.
Kim KH, Gwak HS. Effects of vehicles on the percutaneous absorption of donepezil hydrochloride across the excised hairless mouse skin. Drug Dev Ind Pharm. 2011;37(9):1125-30.
Rhee YS, Huh JY, Park CW, Nam TY, Yoon KR, Chi SC, et al. Effects of vehicles and enhancers on transdermal delivery of clebopride. Arch Pharm Res. 2007;30(9):1155-61.
Touitou E, Levi-Schaffer F, Shaco-Ezra N, Ben-Yossef R, Fabin B. Enhanced permeation of theophylline through the skin and its effect on fibroblast proliferation. Int J Pharm. 1991;70(1-2):159-66.
Touitou E, Levi-Schaffer F, Dayan N, Alhaique F, Riccieri F. Modulation of caffeine skin delivery by carrier design: liposomes versus permeation enhancers. Int J Pharm. 1994;103(2):131-6.
Fabin B, Touitou E. Localization of lipophilic molecules penetrating rat skin in vivo by quantitative autoradiography. Int J Pharm. 1991;74(1):59-65.
Ayala-Bravo HA, Quintanar-Guerrero D, Naik A, Kalia YN, Cornejo-Bravo JM, Ganem-Quintanar A. Effects of sucrose oleate and sucrose laureate on in vivo human stratum corneum permeability. Pharm Res. 2003;20(8):1267-73.
Csizmazia E, Erős G, Berkesi O, Berkó S, Szabó-Révész P, Csányi E. Penetration Enhancer effect of sucrose laurate and Transcutol on ibuprofen. J Drug Deliv Sci Technol. 2011;21(5):411-5.
Cazares-Delgadillo J, Naik A, Kalia YN, Quintanar-Guerrero D, Ganem-Quintanar A. Skin permeation enhancement by sucrose esters: a pH-dependent phenomenon. Int J Pharm. 2005;297(1-2):204-12.
Gungor S, Bergisadi N. Effect of penetration enhancers on in vitro percutaneous penetration of nimesulide through rat skin. Pharmazie. 2004;59(1):39-41.
Barakat NS. Evaluation of glycofurol-based gel as a new vehicle for topical application of naproxen. AAPS PharmSciTech. 2010;11(3):1138-46.
Javadzadeh Y, Hamishehkar H. Enhancing percutaneous delivery of methotrexate using different types of surfactants. Colloids Surf B Biointerfaces. 2011;82(2):422-6.
Senyigit T, Padula C, Ozer O, Santi P. Different approaches for improving skin accumulation of topical corticosteroids. Int J Pharm. 2009;380(1-2):155-60.
Berkó S, et al. Monitoring of skin penetration and absorption with a new in vivo experimental model. Farmacia. 2014;62(6):1157-63.
Tiossi RF, et al. In vitro and in vivo evaluation of the delivery of topical formulations containing glycoalkaloids of Solanum lycocarpum fruits. Eur J Pharm Biopharm. 2014;88(1):28-33.
Ritschel WA, Barkhaus JK. Use of sorption promoters to increase systemic absorption of coumarin from transdermal drug delivery systems. Arzneimittelforschung. 1988;38(12):1774-7.
Ritschel WA, Barkhaus JK. Feasibility study for transdermal delivery of meperidine. Methods Find Exp Clin Pharmacol. 1988;10(7):461-5.
Shaaya AN, Kraus C, Bauman DH, Ritschel WA. Pharmacokinetics and bioavailability of papaverine HCl after intravenous, intracorporeal and penis topical administration in beagle dogs. Methods Find Exp Clin Pharmacol. 1992;14(5):373-8.
Rougier A, Dupuis D, Lotte C Roguet R, , & H. Schaefer (1983) In vivo correlation between stratum corneum reservoir function and percutaneous absorption. J Invest Dermatol 81(275-278):275, 278.
Sutton et al., "Characterization of a Liquid Crystal Stabilized Pharmaceutical Oil-in-Water Emulsion Optimized for Skin Delivery", Journal of Cosmetics, Dermatological Sciences and Applications, vol. 8, No. 4, Dec. 2018.
V. Koprda et al., Skin Penetration Studies of Transcutol Using Radiotracer Technique, GRC (1995), 10 pgs.
Notification of Reasons for Rejection issued in JP2020-567451 dated Nov. 24, 2023, 9 pgs. with translation.
T. Gao, et al., "Sunscreen Formulas with Multilayer Lamella Structure," Cosmetics & Toiletries, vol. 118, pp. 41-52 (Oct. 2003).
D.Y.M. Leung, et al., "New Insights into Atopic Dermatitis," J. Clin. Invest., vol. 113, pp. 651-657 (2004).
L. Kircik, "Topical Treatment Adherence for Psoriasis," Skin Therapy Letter—Family Practice Edition, vol. 4, No. 2, pp. 4 & 5 (2008).
S.R. Feldman, et al., "Psoriasis: Improving Adherence to Topical Therapy," J. Am. Acad. Dermatol., vol. 59, pp. 1009-1016 (2008).
S.M. Ali, et al., "Skin pH: From Basic Science to Basic Skin Care," Acta Derm. Venereal., vol. 93, pp. 261-267 (1-9), Tbl. SI (2013).
Study NCT01856764, "Topical Roflumilast in Adults with Atopic Dermatitis," sponsored by Takeda, available at https://clinicaltrials.gov/ (Jul. 2015).
Y. Javadzadeh, et al., "Transcutol® (Diethylene Glycol Monoethyl Ether): A Potential Penetration Enhancer," Ch. 12, pp. 195-205, in N. Dragicevic, et al., eds., Percutaneous Penetration Enhancers Chemical Methods in Penetration Enhancement: Modification of the Stratum Corneum (2015).
FDA, Inactive Ingredient Guide (Jan. 1996).
M.J. O'Neil, et al., eds., The Merck Index, pp. 2822, 8379 (15th ed., 2013).
Labeling for ELOCON® (mometasone furoate) Cream (2013).
Labeling for DALIRESP® (roflumilast) Tablets (2013).
Physicians' Desk Reference, pp. 305, 748-52, 1432-35 (67th/2013 ed., 2012).
I.M. Rosenstock, "Understanding and Enhancing Patient Compliance with Diabetic Regimens," Diabetes Care, vol. 8, pp. 610-616 (1985).
J. Urquhart, "The Electronic Medication Event Monitor: Lessons for Pharmacotherapy," Clin. Pharmacokinet., vol. 32, pp. 345-356 (1997).
S.S. Zaghloul, et al., "Objective Assessment of Compliance with Psoriasis Treatment," Arch. Dermatol., vol. 140, pp. 408-414 (2004).
P. Assawasuwannakit, et al., "Quantification of the Forgiveness of Drugs to Imperfect Adherence," CPT Pharmacometrics Syst. Pharmacol., vol. 4, e4, pp. 1-8 (2015).
Office Action issued in U.S. Appl. No. 18/057,777 dated Feb. 15, 2024 (25 pages).
Office Action issued in U.S. Appl. No. 18/345,692 dated Oct. 26, 2023 (68 pages).
Office Action issued in U.S. Appl. No. 18/345,732 dated Jan. 24, 2024 (12 pages).
Office Action issued in U.S. Appl. No. 18/345,760 dated Oct. 26, 2023 (19 pages).

* cited by examiner

A. Change from baseline in TPSS×TPA (primary efficacy endpoint)

B. Change from baseline in TPSS (secondary efficacy endpoint)

C. Change from baseline in TPA (secondary efficacy endpoint)

ROFLUMILAST FORMULATIONS WITH AN IMPROVED PHARMACOKINETIC PROFILE

This application is a continuation of U.S. Ser. No. 17/155,679 filed Feb. 5, 2021, which is a continuation in part of U.S. Ser. No. 17/102,056 filed Nov. 23, 2020, which is a continuation of U.S. Ser. No. 16/136,804 filed Sep. 20, 2018, which issued as U.S. Pat. No. 10,940,142 issued on Mar. 9, 2021, which is a continuation of U.S. Ser. No. 15/848,505 filed Dec. 20, 2017, which issued as U.S. Pat. No. 10,105,354 issued on Oct. 23, 2018, which is a continuation of U.S. Ser. No. 15/676,356 filed Aug. 14, 2017, which issued as U.S. Pat. No. 9,884,050 issued on Feb. 6, 2018, which is a divisional of U.S. Ser. No. 15/616,409 filed Jun. 7, 2017, which issued as U.S. Pat. No. 9,895,359, issued Feb. 20, 2018, the disclosures of which are incorporated herein in their entirety by reference.

FIELD OF THE INVENTION

The invention pertains to methods for treating a patient having a disorder that is responsive to treatment with PDE-4 inhibition by the topical administration of a roflumilast formulation having a roflumilast release profile that produces in the patient a flattened plasma concentration time curve and a reduced Cmax relative to administration of an equivalent amount of roflumilast in an oral composition. The methods of treatment of this invention provide a sufficiently high area under the plasma-roflumilast concentration curve (AUC) to attain a systemically effective level of roflumilast without rapid-onset peak plasma concentration (Cmax) (i.e., short Tmax). It has been discovered that these pharmacokinetic characteristics result in a reduction of undesirable side effects associated with oral roflumilast therapy.

BACKGROUND OF INVENTION

Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen-induced skin disorders including psoriasis, seborrheic dermatitis, and atopic dermatitis), and generalized inflammations in the gastrointestinal region (Crohn's disease and ulcerative colitis). Currently, roflumilast is approved for systemic administration (oral) to treat inflammatory disorders involving the lungs, such as chronic obstructive pulmonary disease (COPD).

Roflumilast and its synthesis were described in U.S. Pat. No. 5,712,298 (the "'298 patent"), incorporated herein by reference.* It has long been recognized that pharmaceutical compounds having phosphodiesterase (PDE)-inhibiting properties, such as roflumilast, are useful for treating inflammatory disorders, including inflammatory dermatoses, such as psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64). Although oral tablets of roflumilast have been commercialized, the low aqueous solubility of the compound has been reported to be only 0.53 mg/l at 21° C. in WO95/01338 (corresponding to the '298 patent and incorporated herein by reference in its entirety). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 1511516B1 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

* Unless otherwise indicated, references incorporated herein by reference are incorporated in their entireties for all purposes.

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin. To assure consistent delivery of the API into or across the skin, it must remain either: 1) dissolved over the shelf life of the topical product, or 2) suspended as particles having unchanged crystal habit and unchanged particle size distribution over the shelf life of the topical product.

The ability of a dissolved active ingredient to permeate the barrier of the skin is determined by its molecular structure. A well-known relationship between molecular structure and skin penetration is that increasing molecular weight decreases the rate that an active crosses the skin (J D Bos, M M Meinardi, Exp Dermatol. 2000 June; 9(3):165-9). Another well-understood relationship is that increasing the octanol-water partition coefficient of a hydrophilic active initially increases the rate that an active permeates the skin, but then decreases skin permeation once the active becomes too lipophilic to partition out of the stratum corneum and into the lower layers of the epidermis (D. W. Osborne and W. J. Lambert, Prodrugs for Dermal Delivery, K. B. Sloane ed., Marcel Dekker, New York 163-178 (1992)). The optimal octanol-water partition coefficient is usually at log P values of 2-3. The rate that an active ingredient crosses into the viable epidermis can be further modified based on the composition of the topical product. Final pH of the formulation may be critical, because dissolved ionized active ingredients typically do not permeate the skin as effectively as active ingredients that do not carry a charge (N. Li, X. Wu, W. Jia, M. C. Zhang, F. Tan, and J Zhang. *Drug Dev Indust Pharm* 38(8)985-994). Functional ingredients such as skin penetration enhancers (D. W. Osborne and J. J. Henke, Pharmaceutical Technology 21(11)58-66(1997)) can be added to the topical product to increase skin permeation. For a dissolved active in the topical product, the closer the drug concentration is to the amount of active required to saturate the drug product, the greater the thermodynamic driving force of the active to cross the skin, i.e. the greater the skin flux of the active. The scientific literature guides formulators on how to increase penetration through the polar route, the nonpolar route, and the intercellular lipid pathway or transfollicular penetration. While these theories and mechanisms are sometimes conflicting, it is generally accepted that the most consistent skin permeation of a drug from a topical product occurs when the active ingredient is dissolved in the formulation. For this reason, formulators generally avoid developing a topical product that will have particles or crystals of the active ingredient precipitate during storage according to labeled storage instructions. Precipitation of the active ingredient can occur for various reasons. Particular active ingredients, when formulated with particular pharmaceutical excipients will tend to form supersaturated solutions. At the time of manufacture, all of the active ingredient will be in solution. After days, weeks, or months, this metastable topical product will equilibrate and active ingredient particles will form. If a topical product contains a volatile solvent such as ethanol, then evaporation of the solvent upon storage could result in precipitation of the active ingredient. A less soluble polymorph (Pudipeddi and Serajuddin, J. Pharm. Sci., 94(5) 929-939 (2005)) may nucleate in the topical product and form active ingredient particles that will not re-dissolve. Other products may be formulated too close to the saturation limit of the active ingredient with the result that minor shifts in storage temperatures will cause precipitation. It should be noted that the dramatic temperature shifts that can occur during shipping are expected to cause the reversible precipitation of the active ingredient. Regardless of the reason, irreversible precipitation of the active ingredient during storage of a topical product can have profound effects on the bioavailability and efficacy of a topical product, because only dissolved active ingredients can penetrate into intact stratum corneum, the outermost layer of epithelium of the skin.

For a suspended active ingredient, properties in addition to molecular structure influence skin permeation. The ratio of dissolved to suspended active ingredient can have a significant influence on the amount of active delivered after topical application. It has been shown that optimal drug delivery can be achieved for particular drugs and particular diseases by utilizing a topical composition that includes a dissolved active ingredient that has the capacity to permeate the stratum corneum layer of the epidermis and become available systemically, along with an active ingredient in a microparticulate state that does not readily cross the stratum corneum of the epidermis (U.S. Pat. No. 5,863,560 hereby incorporated by reference). Another property of a suspended active ingredient that affects its delivery is the distribution of suspended particle size. It has been shown that a 6 micron particle will target the hair follicle and penetrate to a depth of 500 micrometers in a terminal hair. For a suspended particle of 0.75 microns to 1.5 microns in size, the particle penetrates the terminal hair shaft to a depth of 800 micrometers (A Patzelt, F Knorr, U Blume-Peytavi, W Sterry, J Lademann, Drug Discovery Today: Disease Mechanisms, 5(2)2008 pages e173-e181). Thus, for suspended active ingredients, skin permeability depends on the following properties: 1) molecular structure of dissolved active ingredient, 2) particulate/crystalline structure of the suspended active ingredient, 3) particle size of the suspended active ingredient, and 4) particle size distribution of the suspended active ingredient. The ability of a topical product composition to modify the skin permeation is similar for suspended active ingredients and dissolved active ingredients. Because skin permeability is dependent on additional properties of the suspended active ingredients, consistent delivery from topical products containing suspended actives is more difficult to maintain than for topical products containing only dissolved active ingredients.

Consistent delivery of a suspended active ingredient from a topical product is assured by formulation into a product in which the suspended particles do not significantly change in size or amount over the shelf life of the product. Change over time in the ratio of dissolved active ingredient to particulate active ingredient can dramatically change the skin permeation of the active ingredient. The same mechanisms described above (supersaturation, temperature changes, evaporation, polymorphic transformation) that can cause precipitation of dissolved active ingredients can alter the dissolved-to-particulate ratio for suspended active ingredients. Change over time in the particle size or particle size distribution of the dispersed active ingredient can also dramatically change the skin permeation of the active ingredient. Sometimes this change in particle size or particle size distribution can be explained by Ostwald ripening of the particles. Ostwald ripening occurs when small particles in the topical product dissolve and redeposit onto larger particles suspended in the same container of topical product. Over time this phenomenon shifts the particle size distribution toward larger particles at the expense of the smaller particles. Ostwald ripening and precipitation of a less soluble polymorph are two major problems in developing topical products containing suspended actives.

In addition to crystal growth and changes in particle size which can dramatically change the skin permeation of roflumilast, successful treatment can be also affected by side effects which can lead to treatment discontinuation. The prescribing information pertaining to DALIRESP® (oral roflumilast tablets marketed in the U.S.) warns of psychiatric adverse reactions (insomnia, anxiety, depression, suicidal ideation and suicidal behavior), weight loss and gastrointestinal side effects when patients are treated with 500 mcg once daily. Because of the high incidence of gastrointestinal side effects, including severe nausea and diarrhea, the prescribing information pertaining to DALIRESP® instructs that it may be beneficial to take half of the therapeutically effective dose, 250 mcg, once daily for 4 weeks prior to commencing the therapeutically effective dose of 500 mcg per day so as to reduce the rate of treatment discontinuation. The prescribing information for DAXAS® (oral roflumilast tablets marketed outside the U.S.) does not instruct the patient to take a reduced non-therapeutically effective dosage prior to taking the therapeutic dose. However, the prescribing information for DAXAS® does report a high incidence of diarrhea, nausea, and abdominal pain associated with this medication.

When roflumilast is orally administered, the drug is rapidly absorbed, resulting in a sharp spike in plasma concentration. According to documents filed in the FDA, upon initial administration of a roflumilast tablet, a Cmax (peak plasma concentration) of 7.34 mcg/l that spiked at a Tmax (time after administration to reach Cmax) 1 hour after administration occurred with a 500 mcg tablet and a Cmax of 3.99 mcg/l that spiked at a Tmax of 1 hour occurred with a 250 mcg tablet. The spike in Cmax followed a clear dose-response relationship. A similar dose-response relationship was shown for the occurrence of gastrointestinal side effects, suggesting a possibility that these side effects are associated with the spike in Cmax.

When multiple doses of oral roflumilast are administered, exposure follows a "peak to trough" pattern. This pattern results in an episodic variation in blood levels of drug and continued gastrointestinal side effects.

Bolle, U.S. Patent Application Publication No. 2006/0084684 discloses topical formulations of roflumilast, salts of roflumilast, the N-oxide of roflumilast, and salts of the N-oxide. Bolle discloses that such formulations are useful to apply to skin lesions for the local treatment of skin disorders or to administer topically for the systemic treatment of skin disorders and other disorders, such as COPD. Bolle discloses that the systemic effect of topical application of the roflumilast formulations is comparable to that of an oral dosage form. Bolle further discloses, in paragraph 0080 that "Comparison with oral administration shows that, irrespective of the composition of the topical preparation, similar Cmax and AUCs and similar excretions with the urine are achieved."

Although Bolle does not discuss the incidence of side effects that occur following topical administration of the roflumilast formulations, because Cmax with the topical formulations, irrespective of the composition of the topical formulation, is similar to that which is obtained with orally administered formulations, and because side effects are correlated with Cmax and Tmax, it would be expected that administration of the topical formulations of Bolle would cause an incidence of side effects similar to that caused by orally administered formulations.

Although oral tablets of roflumilast have been commercialized, topical and parenteral administration require different formulations due to the low aqueous solubility of the compound which has been reported to be only 0.53 mg/l at 21° C. in WO95/01338 (corresponding to the '298 patent and incorporated herein by reference). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 1511516B1 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

Topical application of potent pharmacological agents like roflumilast has been found to provide superior delivery and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin.

A need exists for a method of treating patients having PDE-4 inhibitor responsive disorders with roflumilast, that results in a therapeutically effective systemic dose, does not result in a spike in Cmax, while still providing a high AUC, and which, therefore, is pharmaceutically efficacious but is associated with a decreased incidence of side effects. Indeed, the absence or reduced side effects allow for therapeutic doses to be administered that provide higher systemic exposures (AUCs) than are possible orally and with greater disease efficacy.

SUMMARY OF THE INVENTION

In accordance with the present invention, an improved method of treating a patient having a disorder responsive to PDE-4 inhibition by administering a PDE-4-inhibiting amount of roflumilast, involves administering the roflumilast topically in a composition having a roflumilast release profile that produces in the patient a flattened plasma concentration time curve and a reduced Cmax relative to oral administration of a PDE4-inhibiting amount of roflumilast. Such disorders include inflammatory disorders such as inflammatory dermatoses, including psoriasis, atopic dermatitis and seborrheic dermatitis. As used herein, a disorder is responsive to PDE-4 inhibition if such inhibition results in a prevention of the disorder or a diminution of its severity, duration or recurrence, such disorders also include inflammatory diseases in a variety of organs, especially the lungs (asthma, COPD). Because of reduced side effects with topical administration due to the above-described pharmacokinetics (PK) findings, it may be possible to provide higher systemic exposures (AUCs) with topical administration, resulting in greater therapeutic efficacy than with the oral route of administration.

In a preferred embodiment, the topically applied composition contains from about 0.1% w/w to about 0.5% w/w roflumilast. In a preferred embodiment, the topically applied composition is in the form of a cream or a foam.

In a preferred embodiment, the composition has a roflumilast release profile that results in a reduced Cmax, longer Tmax and flattened plasma concentration time curve relative to that achieved with oral administration of an effective amount of roflumilast in an oral composition marketed under the trademarks DALIRESP® and DAXAS®.

It has been discovered that topical roflumilast compositions having the above-described PK properties produce reduced gastrointestinal, psychiatric, and weight loss side effects as compared to prior art orally administered compositions.

Thus, in another embodiment, the present invention provides a method of treating a patient suffering from a disorder that can be treated by PDE-4 inhibition that comprises: administering a topical pharmaceutical composition comprising 0.5% w/w of roflumilast and a pharmaceutically acceptable carrier, wherein administration of said composition results in reduced gastrointestinal and other side effects relative to oral administration of roflumilast in a composition of roflumilast marketed under the trademark DALIRESP® or DAXAS®.

BRIEF DESCRIPTION OF THE DRAWINGS

FIG. 11a shows Sample 36-1 roflumilast particles precipitated in a cream composition with diethylene glycol monoethyl ether (DEGEE) and without hexylene glycol. The three largest roflumilast particles were measured (0.07 mm×0.09 mm; 0.06 mm×0.06 mm; and 0.10 mm×0.05 mm) and found to have a mean surface area of 5,000 square microns. FIG. 11b shows Sample 36-2 roflumilast particles precipitated in a cream composition with both diethylene glycol monoethyl ether (DEGEE) and hexylene glycol. The three largest roflumilast particles were measured (0.05 mm×0.03 mm; 0.05 mm×0.03 mm and 0.05 mm×0.03 mm) and found to have a mean surface area of 1,500 square microns.

DETAILED DESCRIPTION OF THE INVENTION

Figure 1:
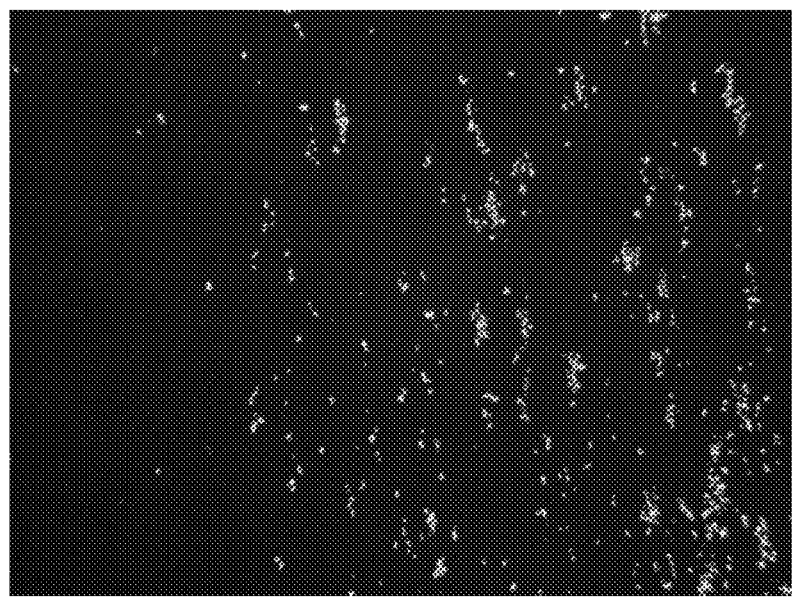
FIG. 1 shows Sample 19-2 "dry" roflumilast crystals from ferrer-Interquim S.A. Batch A14367P, the drug substance used in all the examples in this specification. The roflumilast crystals are 0.01 mm-0.02 mm in length.

The term "roflumilast" as used in this application refers to roflumilast, its salts, the N-oxide of roflumilast, and its salts unless specified otherwise or unless it is clear in context that reference is to roflumilast itself. The terms "N-oxide of roflumilast" and "salts of either roflumilast or of the N-oxide of roflumilast" refer specifically to the N-oxide or salts of either roflumilast or the N-oxide thereof. Roflumilast formulations can be prepared by methods known in the art (e.g. see the '298 patent and U.S. application Ser. No. 14/075, 035).

Roflumilast is a compound of the formula (I)

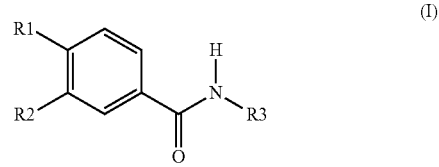

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamid-e (INN: roflumilast).

The term "salts", when referring to roflumilast or the N-oxide of roflumilast, means a salt as described in paragraphs [0012] and [0013] of U.S. Patent Application Publication No. US 2006/0084684, the disclosure of which is incorporated herein by reference.

Hexylene glycol (PharmaGrade. USP/NF) is 2-methyl-2, 4-pentanediol of the formula (II).

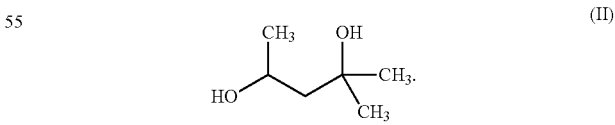

One aspect of present invention is directed to the addition of hexylene glycol to a roflumilast-containing pharmaceutical composition that contains a pharmaceutically acceptable solvent, including water, to inhibit growth of roflumilast crystals in the composition. For topical products designed to contain suspended roflumilast particles or crystals, the addition of hexylene glycol to a composition containing roflumilast, will inhibit (i.e., prevent or substantially reduce in comparison to compositions that do not contain a hexylene glycol) changes in particle size distribution over the shelf life of the product and assure consistent bioavailability. For topical products designed to have roflumilast completely dissolved, hexylene glycol inhibits the growth of precipitated roflumilast particles.

Drug products that have fully dissolved drug substance for the labeled storage conditions over product shelf life will have the active precipitate if the product is formulated to maintain significant thermodynamic driving force. Typical storage conditions for a topical pharmaceutical cream are: Store at room temperature: 60° F./15° C.-80° F./26° C. Do not freeze. It is understood by product development scientists and regulatory agency reviewers that a topical product will not always be stored over this temperature range. Therefore, the FDA requires that all topical products undergo freeze-thaw cycling and temperature excursion studies. The active is neither required nor expected to remain in solution when the product is exposed to temperatures of −20° C., dramatically below 15° C. (60° F.) of the labeled storage condition. Since topical products containing completely dissolved drug are usually formulated near saturation, i.e. near maximum thermodynamic driving force, most topical products experience precipitation of the active ingredient during freeze-thaw cycling or temperature excursion studies. The addition of hexylene glycol prevents crystal growth of roflumilast when precipitation occurs due to temperature excursions below the labeled storage conditions. Inhibiting crystal growth assures that any precipitated active will quickly return to being completely dissolved once the product is returned to controlled room temperature. The prompt return of the precipitated roflumilast to a fully dissolved state assures consistent, reproducible bioavailability, efficacy and safety of the topically applied product. Hexylene glycol can be added between 0.1% and 20% on a weight/weight basis, preferably between 0.25% and 8% on a weight/weight basis and most preferably between 0.5% and 2% on a weight/weight basis.

The topical roflumilast product formulations that benefit from the addition of hexylene glycol include but are not limited to aerosols, foams, sprays, emulsions (which can also be called creams, lotions, or ointments), gels (two phase or single phase), liquids, ointments, pastes, shampoos, suspensions, and systems. These are the tier two terms within compendia taxonomy for dosage forms containing pharmaceutical active ingredients (US Pharmacopeia <1151>).

In a second aspect of the present invention, it has been unexpectedly discovered that, in direct contrast to the dogma of the prior art, a pharmaceutical formulation, such as a topically applied pharmaceutical formulation containing roflumilast, provides an altered PK (pharmacokinetic) profile with a reduced Cmax or a reduced absorption rate to reach Cmax when the formulations contain one or more phosphate ester surfactants compared to pharmaceutical formulations containing roflumilast without a phosphate ester surfactant(s). In particular, it has been unexpectedly discovered that a pharmaceutical formulation containing roflumilast and one or more phosphate ester surfactants, when topically administered to an individual, provides a systemically effective level of the PDE-4 inhibitor comparable to, or even greater than, that achieved with oral administration by slow absorption and without a Cmax spike of the PDE-4 inhibitor into the bloodstream.

In pharmacokinetic terms, a formulation containing roflumilast, and a phosphate ester surfactant, when administered to an individual, such as by applying topically to the skin of an individual, provides a sufficiently high Area Under the Curve (AUC) to attain a systemically effective level of roflumilast without rapidly producing a peak plasma concentration (Cmax) that is associated with gastrointestinal side effects. That is, the absorption rate of the drug to reach Cmax is decreased when the formulation of the present application is administered, compared with the administration of formulations of the prior art.

As used herein, the term "absorption rate to reach Cmax" means the slope of the PK curve between the administration of a formulation containing drug until Cmax, or the slope of the PK curve between a trough and the adjacent peak following serial multiple dose administrations of the formulation.

Thus, in contrast to the teachings of the prior art, the formulations of the present application unexpectedly have a markedly different PK profile compared to prior art formulations containing roflumilast. The formulations of the present application provide a sufficiently high AUC to attain a systemically effective level of roflumilast without producing a spike in Cmax. The gradual ascent to Cmax obtained following topical application of the formulations of the present invention is markedly different from that of prior art formulations, but the AUC is similar. Additionally, following multiple doses of the formulation, the PK profile lacks the initial Cmax spike and the peak to trough pattern that is obtained following multiple daily dosing with prior art formulations containing the drug.

This discovery provides several unexpected advantages. Primarily, it provides a means for treatment of medical conditions that are responsive to the administration of roflumilast, while minimizing the incidence of undesirable side effects, especially GI side effects. This in turn leads to greater patient compliance and reduced incidence of cessation of treatment due to the development of such side effects.

Furthermore, because the ascent to Cmax is relatively slow, and a rapid Cmax spike is avoided, the formulations of the present invention can result in higher systemic exposure levels (AUC) than are possible with prior art formulations and without the side effects associated with a Cmax spike, such as those of the G.I. system. Such previously unobtainable exposure levels will provide a greater efficacy in the treatment of diseases.

Moreover, it has been unexpectedly discovered that, following the attainment of Cmax after administration, there is a very flat and prolonged plateau in blood levels of the drug. Additionally, the PK profile obtained after multiple doses of the formulation of the present application is extremely and unexpectedly flat and prolonged with an extremely small peak to trough fluctuation following administration for 28 days. This flatness of the PK profile is especially pronounced when the formulation further contains diethylene glycol monoethyl ether.

Because the absorption of roflumilast from the formulation in an amount required to provide a therapeutic effect is not dependent on a spike in absorption to provide a high Cmax and because the absorption of roflumilast is stable and has a flat PK profile, an individual user of a formulation producing such a PK profile may miss one or more doses from time to time and still maintain efficacy of the treatment.

An important advantage of the present invention is that, a slow ascent to Cmax without a concomitant Cmax spike permit the obtaining of higher systemic exposure levels (AUC) than are possible with prior art formulations and without the side effects associated with Cmax spike, such as those of the G.I. system. Such previously unobtainable exposure levels will provide a greater efficacy in the treatment of diseases.

A pharmaceutical formulation of the present invention contains roflumilast in a concentration which is sufficient to ameliorate a medical condition that is responsive to the administration of a PDE-4 inhibitor drug, such as psoriatic arthritis, psoriasis, atopic dermatitis, asthma and COPD. The concentration of roflumilast, in the formulation is that which is sufficient to obtain a desired systemic pharmacologic effect when the formulation is applied to the skin of an individual. This concentration will necessarily differ based on the type of formulation and the disease or condition to be treated. The concentration of roflumilast within the formulation is typically in the range of 0.001 to 25% w/w, with a preferred range between 0.01 to 5%, a more preferred range between 0.05 and 1%, and a most preferred range between 0.1 and 0.5%. In a particular preferred embodiment, the concentration of roflumilast in the formulation is between 0.05 and 0.5%, such as 0.05%, 0.15%, 0.3%, and 0.5% w/w.

The formulation may contain a means for inhibiting crystal growth and changes in particle size distribution which can be hexylene glycol. The formulation may further contain a means for providing a sufficiently high AUC to attain a systemically effective level of roflumilast without producing a spike in Cmax, which can be one or more phosphate ester surfactants. Examples of phosphate ester surfactants that may be included in the formulations of this application include but are not limited to potassium cetyl phosphate, potassium C9-15 alkyl phosphate, potassium C11-15 alkyl phosphate, potassium C12-13 alkyl phosphate, potassium C12-14 alkyl phosphate, potassium lauryl phosphate, C8-10 alkyl ethyl phosphate, C9-15 alkyl phosphate, C20-22 alkyl phosphate, castor oil phosphate, ceteth-10 phosphate, cetheth-20 phosphate, ceteth-8 phosphate, cetearyl phosphate, cetyl phosphate, dimethicone PEG-7 phosphate, disodium lauryl phosphate, disodium oleyl phosphate, lauryl phosphate, myristyl phosphate, octyldecyl phosphate, oleth-10 phosphate, oleth-5 phosphate, oleth-3 phosphate, oleyl ethyl phosphate oleyl phosphate, PEG-26-PPG-30 phosphate, PPG-5 ceteareth-10 phosphate, PPG-5 ceteth-10 phosphate, sodium lauryl phosphate, sodium laureth-4 phosphate, steartyl phosphate, DEA-cetyl phosphate, DEA-oleth-10 phosphate, DEA-oleth-3 phosphate, DEA-C8-C18 perfluoroalkylethyl phosphate, dicetyl phosphate, dilaureth-10 phosphate, dimyristyl phosphate, dioleyl phosphate, tricetyl phosphate, triceteareth-4 phosphate, trilaureth-4 phosphate, trilauryl phosphate, triolyeyl phosphate and tristearyl phosphate.

The concentration of the phosphate ester surfactant in the formulation is that which is sufficient to produce a stable emulsion having uniform globule size. If desired, lower concentrations of the phosphate ester surfactant may be combined with other emulsifiers to produce a stable emulsion having uniform globule size. The phosphate ester surfactant may also increase the solubility of the roflumilast in the cream. The concentration of the phosphate ester surfactant generally may be any concentration between 1.0% to 25% w/w. The preferred concentration can be different for different administration forms. In a preferred embodiment, when the formulation is a cream or ointment, the concentration of the phosphate ester surfactant is between 2.5% and 20%, with a more preferred concentration range between 5% and 15%, and a most preferred concentration being about 10% w/w. When the formulation is in the form of a foam, the concentration is preferably between 1.0%-10%, more preferably between 1.0%-10%, and most preferably 2%.

The formulation can optionally contain, a means for increasing the solubility of roflumilast, which can be diethylene glycol monoethyl ether. Diethylene glycol monoethyl ether is also known as 2-(2-ethoxyethoxy)ethanol, or as DEGEE, and is marketed under the several tradenames, including TRANSCUTOL® (Gattefosse Corporation, Paramus, NJ), CARBITOL™ (The Dow Chemical Company, Midland, MI), DIOXITOL® (Shell Oil Company, Houston, TX), and POLY-SOLV DM (Monument Chemical, Houston, TX).

DEGEE is often added to topical products as a co-solvent to increase solubility of the drug in the formulation. Addition of DEGEE to a topical formulation has also been shown to enhance skin penetration, i.e. increase Cmax, of topically administered pharmaceutical actives. See D. W. Osborne and J. Musakhanian, "Skin Penetration and Permeation Properties of TRANSCUTOL®—Neat or Diluted Mixtures", AAPS Pharm SciTech. 19(8):3512-3533 (2018) DOI: 10.1208/s12249-018-1196-8; and Javadzadeh et al, Chapter 12 pages 195-205, in Percutaneous Penetration Enhancers Chemical Methods in Penetration Enhancement: Modification of the Stratum Corneum (N. Dragicevic, H. I. Maibach, eds) Springer-Verlag Berlin Heidelberg 2016.

The concentration of the diethylene glycol monoethyl ether, if present, in the formulation is that which is sufficient to dissolve the active pharmaceutical ingredient. Diethylene glycol monoethyl ether may also enhance the skin penetration of the roflumilast. Generally, the concentration of the diethylene glycol monoethyl ether is between 5% and 50% w/w, with a preferred range of concentrations between 10% and 40% w/w, a more preferred range between 15% and 30% w/w, and a particular preferred concentration being about 15-25% w/w. Likewise, water is formulated as about 20-90% (w/w) in topical products. For blends of DEGEE and water the ratio can range from 1:10 to 20:1. Preferably the DEGEE:water ratio is 1:4 to 9:1 in a formulation containing roflumilast. Generally, DEGEE-water blends can be used to dissolve up to 2.0% roflumilast (in the finished product) or preferably up to 0.5% roflumilast (in the finished product).

The formulation for topical application to the skin is preferably a semi-solid dosage form that is cosmetically acceptable for use on the skin and which is easily spreadable on the skin. Examples of such semi-solid dosage forms include emulsions, ointments, creams, gels, and pastes. The formulation may alternatively be in a form other than a semi-solid dosage form, such as a liquid, which may be administered as a spray, or a foam. Preferably, a formulation for topical administration is in one of the following forms:

An oil-in-water emulsion: The product may be formulations in which hexylene glycol is added to an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be formulations in which roflumilast is incorporated into an emulsion that includes a continuous hydrophobic phase and an aqueous phase that includes the DEGEE-water blend and optionally one or more polar hydrophilic carrier(s) as well as salts or other components. These emulsions may include oil-soluble or oil-swellable polymers as well as one or more emulsifier(s) that help to stabilize the emulsion.

For both oil-in-water and water-in-oil emulsions, order of addition may be important. Roflumilast can be added pre-dissolved in the continuous aqueous phase containing the DEGEE-water blend. Likewise, roflumilast can be pre-dissolved in the hydrophobic discrete phase of the emulsion that is then mixed with the DEGEE-water blend and optional hydrophilic excipients that do not contain the active ingredient. Roflumilast can be pre-dissolved in both the oil phase and water phase of the emulsion or added pre-dissolved in DEGEE or a DEGEE-water blend after the emulsion has been formed. Some emulsions undergo phase inversion over a specific temperature range during cooling of the emulsion. Thus, roflumilast may be added to a water-in-oil emulsion above the phase inversion temperature, with the final drug product being an oil-in-water emulsion at controlled room temperature, or vice versa.

Thickened Aqueous gels: These systems include the DEGEE-water blend with dissolved roflumilast and optionally one or more polar hydrophilic carrier(s) such as hexylene glycol which has been thickened by suitable natural, modified natural, or synthetic thickeners such as described below. Alternatively, the thickened aqueous gels can be thickened using suitable polyethoxylate alky chain surfactants or other nonionic, cationic, or anionic systems.

Thickened Hydroalcoholic gels: These systems include a blend of water and alcohol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

Hydrophilic gels: These are systems in which the continuous phase includes at least one water soluble or water dispersible hydrophilic component other than water. The formulations may optionally also contain water up to 60% by weight. Higher levels may be suitable in some compositions. Suitable hydrophilic components include one or more glycols such as polyols such as glycerin, propylene glycol, butylene glycols, polyethylene glycols (PEG), random or block copolymers of ethylene oxide, propylene oxide, and/or butylene oxide, polyalkoxylated surfactants having one or more hydrophobic moieties per molecule, silicone copolyols, blend of ceteareth-6 and stearyl alcohol as well as combinations thereof, and the like.

A hydrophilic or hydrophobic ointment: The compositions are formulated with a hydrophobic base (e.g. petrolatum, thickened or gelled water insoluble oils, and the like) and optionally having a minor amount of a water soluble phase. Hydrophilic ointments generally contain one or more surfactants or wetting agents Solvents Compositions according to the present invention may include a means for obtaining the desired level of active ingredient solubility in the topical product which can be one or more solvents or co-solvents. The solvent may also modify skin permeation or the activity of other excipients contained in the formulation. Means for obtaining the desired level of active ingredient solubility in the topical product include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, polyethylene glycol, glycerol, propylene glycol and SD alcohol.

Moisturizers

Compositions according to the present invention may include a moisturizer to increase the level of hydration. For emulsions, the moisturizer is often a component of the discrete or continuous hydrophobic phase. The moisturizer can be a hydrophilic material including humectants or it can be a hydrophobic material including emollients. Suitable moisturizers include but are not limited to:1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, light mineral oil, lanolin limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, sorbitol, stearic acid, urea and stearyl alcohol.

Surfactants and Emulsifiers

Compositions according to the present invention optionally can include one or more surfactants to emulsify the composition and to help wet the surface of the actives or excipients. As used herein the term "surfactant" means an amphiphile (a molecule possessing both polar and nonpolar regions which are covalently bound) capable of reducing the surface tension of water and/or the interfacial tension between water and an immisicible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-10 phosphate, ceteth-2, ceteth-20, ceteth-23, choleth-24, cocamide ether sulfate, cocamine oxide, coco betaine, coco diethanolamide, coco monoethanolamide, coco-caprylate/caprate, dicetyl phosphate, disodium cocoamphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax.

Phosphate ester surfactants can also act as a means for reducing a spike in Cmax while producing an AUC sufficient to attain a systemically effective level of roflumilast. Suitable phosphate ester surfactants include but are not limited to potassium cetyl phosphate, potassium C9-15 alkyl phosphate, potassium C11-15 alkyl phosphate, potassium C12-13 alkyl phosphate, potassium C12-14 alkyl phosphate, potassium lauryl phosphate, C8-10 alkyl ethyl phosphate, C9-15 alkyl phosphate, C20-22 alkyl phosphate, castor oil phosphate, ceteth-10 phosphate, cetheth-20 phosphate, ceteth-8 phosphate, cetearyl phosphate, cetyl phosphate, dimethicone PEG-7 phosphate, disodium lauryl phosphate, disodium oleyl phosphate, lauryl phosphate, myristyl phosphate, octyldecyl phosphate, oleth-10 phosphate, oleth-5 phosphate, oleth-3 phosphate, oleyl ethyl phosphate oleyl phosphate, PEG-26-PPG-30 phosphate, PPG-5 ceteareth-10 phosphate, PPG-5 ceteth-10 phosphate, sodium lauryl phosphate, sodium laureth-4 phosphate, steartyl phosphate, DEA-cetyl phosphate, DEA-oleth-10 phosphate, DEA-oleth-3 phosphate, DEA-C8-C18 perfluoroalkylethyl phosphate, dicetyl phosphate, dilaureth-10 phosphate, dimyristyl phosphate, dioleyl phosphate, tricetyl phosphate, triceteareth-4 phosphate, trilaureth-4 phosphate, trilauryl phosphate, triolyeyl phosphate and tristearyl phosphate.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, carboxy vinyl copolymer, carboxymethylcellulose, carboxypolymethylene, carrageenan, guar gum, hydroxyethyl cellulose, hydroxypropyl cellulose, microcrystalline wax, and methylcellulose.

The formulation may contain one or more thickening agent to provide viscosity so that the formulation may be provided in the form of a semisolid, such as a lotion, gel, cream, or ointment. Examples of suitable thickening agents include but are not limited to soluble, swellable, or insoluble organic polymeric thickeners such as natural and synthetic polymers or inorganic thickeners including but not limited to acrylates copolymer, carbomer 1382, copolymer type B, carbomer homopolymer type A, homopolymer type B, carbomer homopolymer type C, carboxypolymethylene, carrageenan, guar gum, hydroxyethyl cellulose, hydroxypropyl cellulose, microcrystalline wax, acacia, alginic acid, bentonite, carbomers, also known as carboxy vinyl polymers, such as sold under the tradename Carbopol® (Lubrizol, Wickliffe, Ohio), carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum. The thickening agent may reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

Additional Components

Compositions according to the present invention may be formulated with additional components such as fillers, carriers and excipients conventionally found in cosmetic and pharmaceutical topical products. Additional components including but not limited to foaming agents, propellants preservatives (e.g. p-hydroxybenzoic esters, benzyl alcohol, phenylmercury salts, chlorocresol), antioxidants, sequestering agents, stabilizers, buffers, pH adjusting solutions, skin penetration enhancers, film formers, dyes, pigments, diluents, bulking agents, fragrances and other excipients to improve the stability or aesthetics of the product, may be added to the composition.

The formulation may contain other pharmaceutically acceptable excipients if desired. For example, the formulation may contain a humectant such as glycerin, sorbitol, hexylene glycol, urea, or propylene glycol. The formulation may contain an emollient such as petrolatum, lanolin, mineral oil, light mineral oil, stearic acid, cyclomethicone, or dimethicone. Additional optional excipients include stabilizers, foaming agents, preservatives such as methylparaben, pH adjusting agents such as sodium hydroxide, chelating agents such as EDTA and its salts, and buffers.

In one preferred embodiment, the roflumilast is in the form of an aerosolized foam which is particularly suitable for application to the scalp. Any suitable propellant can be used to prepare the aerosolized foam. Particularly preferred propellants are Isobutane A-31, Aeropin 35, Butane 48, Dimethyl Ether/N-Butane-(53/47), Propane/Iso-Butane/N-Butane, Propane/lsobutane-A70, and Propane/Isobutane A-46, N-Butane A-17.

Additional Active Agents

Compositions according to the present invention may be formulated with additional active agents depending on the condition being treated. The additional active agents include but are not limited to NSAIDs (e.g. Aspirin, Ibuprofen, Ketoprofen, Naproxen), Apremilast and other PDE4 inhibitors, JAK inhibitors (e.g. Tofacitinib, Ruxolitinib, Oclacit), leukotriene inhibitors (e.g. Zileuton, Zafirlukast, Montelukast), mast cell stabilizers (e.g. Nedocromil, Cromolyn sodium, Ketotifen, Pemirolast), Anthralin (dithranol), purine synthesis inhibitors (e.g. Azathioprine), Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), retinoids (e.g., Acitretin, Tazarotene), calcineurin inhibitors (eg, cyclosporine, tacrolimus, pimecrolimus), Resorcinol, Colchicine, bronchodilators (e.g. beta-agonists, anticholinergics, theophylline), and antibiotics and other anti-infectives (e.g. erythromycin, ciprofloxacin, metronidazole, and anti-fungals such as miconazole and terbinafine).

Administration and Dosage

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains a means for inhibiting crystal growth and changes in particle size which is preferably hexylene glycol in an amount of between 0.1% and 20% w/w, more preferably between 0.25% and 8% w/w and most preferably between 0.5% and 2% w/w.

The composition preferably contains one or more phosphate ester surfactants. The concentration of the phosphate ester surfactant generally may be any concentration between 1.0% to 25% w/w.

The composition preferably contains a component for increasing the solubility of roflumilast, which is preferably diethylene glycol monoethyl ether. The concentration of the diethylene glycol monoethyl ether may be any concentration between 5% and 50% w/w.

The topical formulation containing roflumilast, is applied to the skin in an amount that is sufficient to obtain the desired pharmacologic effect, which typically is to ameliorate the signs and/or symptoms of a medical disorder. The amount of the formulation that is applied may vary depending on the concentration of roflumilast within the formulation, and the frequency with which the formulation is applied. Generally, the formulation is applied with a frequency between weekly to several times daily, preferably between every other day to three times daily, and most preferably one or two times daily.

The formulation containing roflumilast may be used in veterinary and in human medicine to treat a systemic medical condition that is ameliorated by or responsive to systemic administration of roflumilast. Non-limiting examples of such medical conditions include but are not limited to acute and chronic airway disorders such as bronchitis, allergic bronchitis, asthma, and COPD; proliferative, inflammatory and allergic dermatoses such as psoriasis, scalp psoriasis, or inverse psoriasis, irritant and allergic contact eczema and other varieties of eczema, hand eczema, atopic dermatitis, seborrheic dermatitis, lichen simplex chronicus, sunburn, aphthous ulcers, lichen planus, vitiligo, pruritus in the genital, anal or other body regions, alopecia areata, hypertrophic scars, discoid lupus erythematosus, follicular and extensive pyodermas, endogenous and exogenous acne, acne rosacea, disorders which are based on an excessive release of TNF and leukotrienes, disorders of the heart which can be treated by PDE inhibitors, inflammations in the gastrointestinal system (including the liver) or central nervous system, disorders of the eye, disorders which can be treated by the tissue-relaxant action of roflumilast and other proliferative, inflammatory and allergic skin disorders; and immune mediated diseases such as arthritis including rheumatoid arthritis, rheumatoid spondylitis, osteoarthritis, and psoriatic arthritis.

The systemic dose of a drug administered topically depends on the concentration in the formulation, on the surface area to which the drug is applied and on the disease/anatomical site being treated. For example, the thick plaques of psoriasis decrease the systemic dose, but cracks and fissures in and around the plaques provide a shunt pathway to increase the systemic dose. These effects tend to cancel each other out so that the systemic dose found after topically treating psoriasis patients over similar Body Surface Areas (% BSA) is similar to the systemic dose obtained in treating normal volunteers. This also results in psoriatic patients tending to have the same systemic dose throughout treatment duration even though their disease is steadily resolving to become clear or nearly clear. When skin afflicted with atopic dermatitis (AD) is treated, there is a much higher systemic dosing for three reasons: (1) AD skin has an inherent skin barrier defect that always results in a higher systemic dose after topical treatment, (2) higher % BSA areas require treatment in AD (>20% BSA) compared to psoriasis (on average 7% BSA) because AD covers more of the body's skin surface area than psoriasis, and 3) psoriasis is primarily a disease of adults while AD is a disease in children. The ratio of skin surface area to body weight is higher in a child compared to an adult.

Pediatric dosing of topical products such as roflumilast cream is much simpler than oral tablets because topical creams do not have rigid dose units, and for children too young to self-administer product, the product does not need to be reformulated for a caregiver to administer the product. The challenge in topically dosing children is that the ratio of skin surface area to body weight changes dramatically from birth to adulthood. This is a major concern when dosing neonates with topical products, but of less concern when dosing children who are at least 3-months old and proportionately less concern when dosing pediatric patients 2 years or older. The ratio of surface area to body weight for pediatric patients compared to an adult is shown below. The greater ratio of skin surface area to body weight corresponds to a lower volume of distribution within the pediatric population after topical administration of the drug product. While the stratum corneum is intact shortly after birth (<1 month), the way human skin stores, and transports water becomes adult-like only after the first year of life (Batchelor, et al., *Formulations for children: problems and solutions,* British Journal of Clinical Pharmacology, 79:3, pp. 405-418 2013. At two years of age, the stratum corneum is still thinner compared to an adult (10 μm compared to 12 μm) and thus barrier function is slightly diminished (Walters, et al., Developmental Changes in Skin Barrier and Structure during the First 5 years of Life, Skin Pharmacol Physiol, 29:111-118, 2016). By the time a child reaches 3-5 years of age the skin barrier is similar to that of an adult.

| Average (50 percentile) BSA and Body Weights in young children of 66 kg and BSA of 17,000 $cm^2$ | | | |
|---|---|---|---|
| Patient Age | Skin Surface Area | Body Weight | Ratio Child to Adult |
| Neonate | 2,100 $cm^2$ | 3.4 kg | 2.4 |
| 3-months | 3,400 $cm^2$ | 6 kg | 2.2 |
| 2-years | 5,000 $cm^2$ | 12.4 kg | 1.6 |

The lower volume of distribution in the very young pediatric population compared to an adult results in children experiencing a higher systemic dose compared to an adult administered the exact same drug concentration applied over the same body surface area afflicted with the same severity of skin disease. A higher systemic dose in children can lead to an increase in adverse events such as psychiatric, weight loss and gastrointestinal side effects. The present formulations for topical application are suitable for administration to atopic dermatitis patients as young as 3 months and psoriasis patients as young as 2 years of age due to a roflumilast release profile that produces a flattened plasma concentration time curve and a reduced Cmax thereby decreasing adverse events in pediatric populations.

The formulation for topical application containing roflumilast, may be prepared by processes typically used in the field of manufacture of pharmaceutical formulations for topical application. In order to make a single-phase formulation, such as a liquid, the constituents of the formulation may be combined and mixed until a homogenous solution or suspension of the active ingredient is obtained. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The one or more drug actives may be dissolved (molecularly dispersed), complexed, or associated with an excipient or other active, or may be particulate (amorphous or crystalline). The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

The following examples are provided to enable those of ordinary skill in the art to make and use the methods and compositions of the invention. These examples are not intended to limit the scope of what the inventor regards as the invention. Additional advantages and modifications will be readily apparent to those skilled in the art.

In the following examples, Crodafos™ CES (Croda Inc., Edison, NJ), containing the phosphate ester surfactants dicetyl phosphate and ceteth-10 phosphate, is utilized as a representative example of phosphate ester surfactants.

EXAMPLE 1

A few mg of roflumilast API (Batch A14367P from Interquim S.A.) dry powder was tapped onto a microscope slide, a coverslip was moved into place and crystal habit and particle size of the API were examined using polarized light microscopy using a 10× objective (FIG. 1, microscope sample 19-2).

Figure 2:
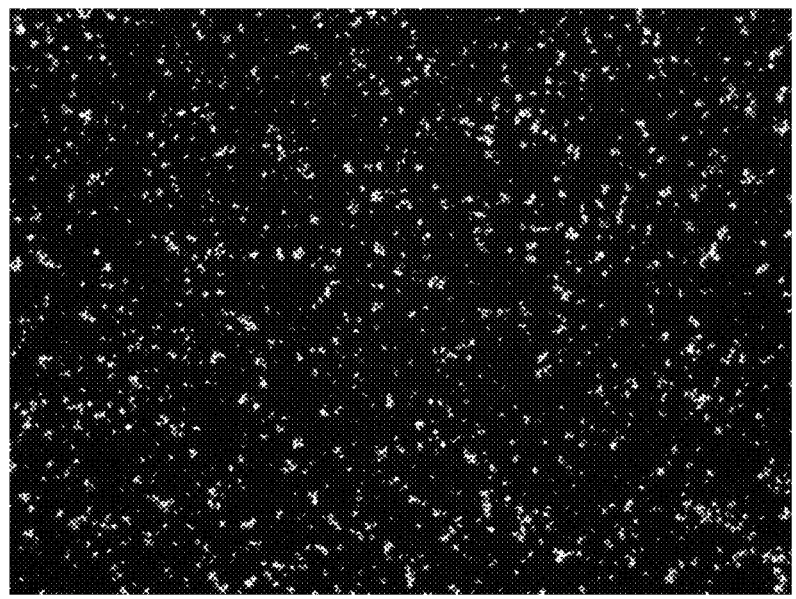
FIG. 2 shows Sample 20-3 roflumilast crystals suspended in equimolar hexylene glycol:water solution after storage for six weeks at room temperature under 10× power. The roflumilast crystals are 0.01 mm-0.02 mm in length.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 10× objective (FIG. 2, microscope sample 20-3).

Figure 3:
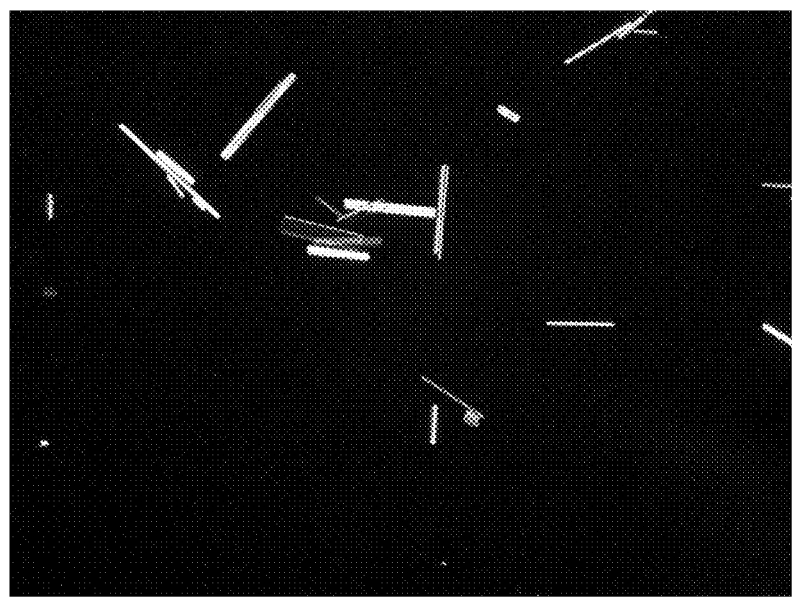
FIG. 3 shows Sample 20-2 roflumilast crystals suspended in equimolar diethylene glycol monoethyl ether:water solution after storage for six weeks at room temperature. The roflumilast crystals are 0.04 mm-0.20 mm in length and 0.01 mm-0.02 mm in width.

0.0111 grams of roflumilast (Batch A14367P from Interquim S.A.) was weighed into a liquid scintillation vial. An equimolar blend of diethylene glycol (DEGEE) (Transcutol P, lot 146063, Gattefosse) and distilled water was added dropwise with mixing to the vial containing roflumilast to produce a suspension of roflumilast in excess of the solubility limit. An equimolar blend is 88.3% DEGEE and 11.7% water on a weight/weight percent basis. After mixing each addition of DEGEE:water blend, the tightly capped vial was returned to a water bath set at 25° C. It required 0.2477 grams of equimolar DEGEE:Water blend to completely dissolve the 0.0111 grams of roflumilast and give a 4.29% roflumilast in equimolar DEGEE:Water (wt/wt %) solution. This sample (labeled 13-1) was a solution of roflumilast at 25° C. and the vial was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 10× objective (FIG. 3, microscope sample 20-2).

EXAMPLE 2

Figure 4:
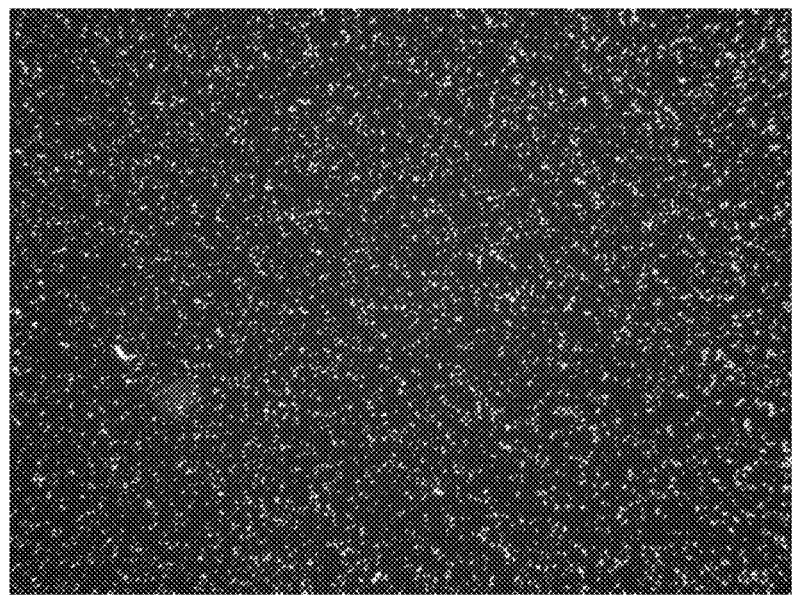
FIG. 4 shows Sample 20-3 roflumilast crystals suspended in equimolar hexylene glycol:water solution after storage for six weeks at room temperature under 4× power. The roflumilast crystals are 0.01 mm-0.02 mm in length.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 4, microscope sample 20-3).

Figure 5:
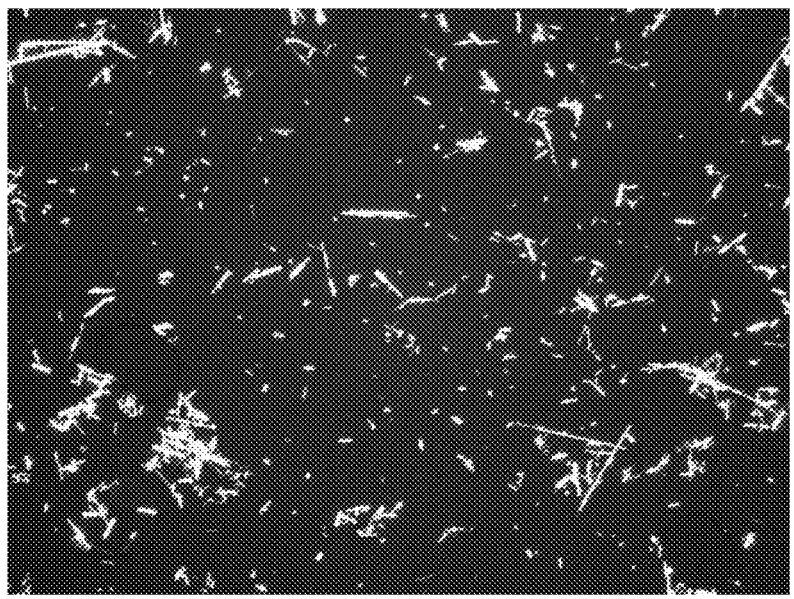
FIG. 5 shows Sample 21-2 roflumilast crystals suspended in equimolar ethanol:water solution after storage for six weeks at room temperature. The roflumilast crystals are 0.05 mm-0.25 mm in length and 0.02 mm in width.

0.0260 grams of roflumilast (Batch A14367P from Interquim S.A.) was weighed into a liquid scintillation vial. 1.0705 grams of an ethanol:water blend (Everclear which is 74.98% ethanol and 25.02% water on a weight/weight percent basis or 95% alcohol by volume) was added to produce a dispersion of roflumilast in an ethanol:water blend in excess of the solubility limit. This sample (labeled as "Alc" page 2) was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 5, microscope sample 20-3).

Figure 6:
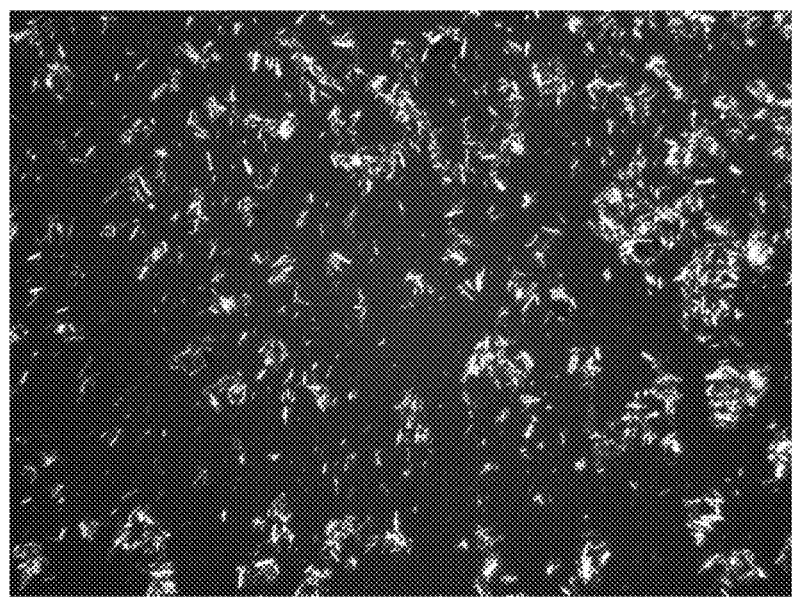
FIG. 6 shows Sample 21-3 roflumilast crystals suspended in equimolar PEG 400:water solution after storage for six weeks at room temperature. The roflumilast crystals are 0.05 mm-0.07 mm in length and 0.02 mm in width.

0.0180 grams of roflumilast (Batch A14367P from Interquim S.A.) was weighed into a liquid scintillation vial. Polyethylene glycol 400 (lot 1DE0880, Spectrum) was added dropwise with mixing to the vial containing roflumilast to produce a suspension of roflumilast in excess of the solubility limit. After mixing each addition of polyethylene glycol 400, the tightly capped vial was returned to a water bath set at 25° C. It required 0.5486 grams of propylene glycol 400 to completely dissolve the 0.0180 grams of roflumilast and give a 3.18% roflumilast in polyethylene glycol 400 solution. This sample (labeled as "PEG 400" page 1) was a solution at 25° C. and was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 6, microscope sample 21-3).

Figure 7:
FIG. 7 shows Sample 21-4 roflumilast crystals suspended in equimolar DMSO:water solution after storage for six weeks at room temperature. The roflumilast crystals are 0.10 mm-0.67 mm in length and 0.02 mm-0.10 mm in width.

0.0103 grams of roflumilast (Batch A14367P from Interquim S.A.) was weighed into a liquid scintillation vial and mixed with 0.2501 grams of dimethyl sulfoxide (lot US150, Gaylord Chemical) to give a 28.5% solution of roflumilast at 25° C. This sample (labeled as "DMSO" page 2) was then stored undisturbed at about 15-18° C., protected from the light for six weeks. A sample of precipitated roflumilast crystals was removed from the vial, placed on a microscope slide (with coverslip) and then examined using polarized light microscopy using a 4× objective (FIG. 7, microscope sample 21-4).

Figure 8:
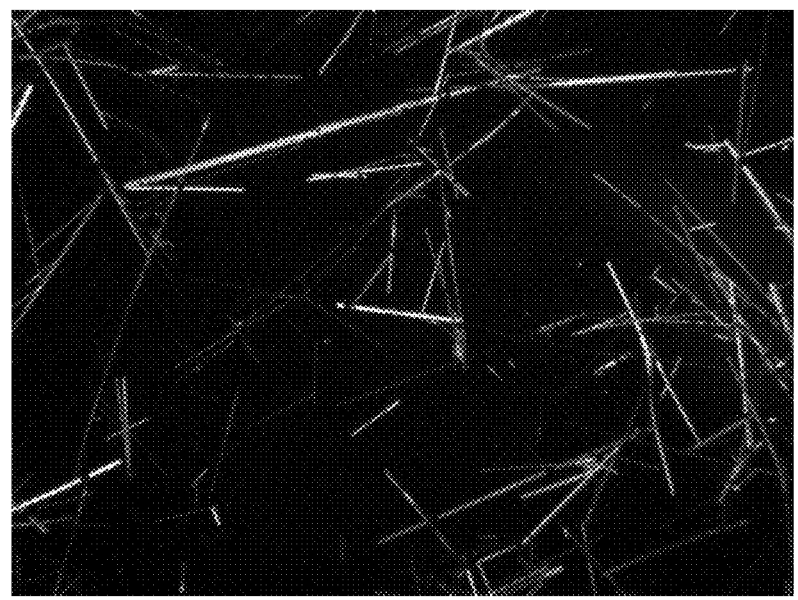
FIG. 8 shows Sample 21-5 roflumilast crystals suspended in equimolar propylene glycol:water solution after storage for six weeks at room temperature. The roflumilast crystals are 0.20 mm-1.60 mm in length and 0.02 mm in width.
Figure 9:
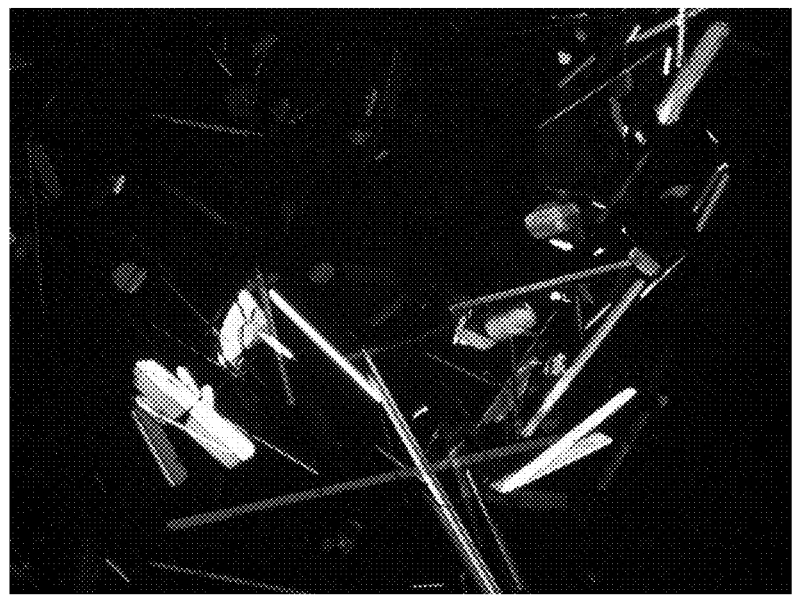
FIG. 9 shows Sample 20-1 roflumilast crystals suspended in equimolar NMP:water solution after storage for six weeks at room temperature. The roflumilast crystals are 0.10 mm-1.55 mm in length and 0.02 mm-0.13 mm in width.

0.0061 grams of roflumilast (Batch A14367P from Interquim S.A.), 1.9332 grams of propylene glycol (lot 1EC0004, Spectrum) and 0.2335 grams distilled water was mixed to initially form a clear solution at 25° C. The composition of the sample was 0.28% roflumilast, 88.97% propylene glycol and 10.75% water on a weight/weight % basis. After 105 minutes of storage at 25° C. a "dusting" of fine roflumilast crystals were observed on the bottom of the vial. Six days later additional crystals had settled to the bottom of the vial. This sample (labeled 7-2) was then stored undisturbed at about 15-18° C., protected from the light for six weeks. A sample of precipitated roflumilast crystals was removed from the vial, placed on a microscope slide (with coverslip) and then examined using polarized light microscopy using a 4× objective (FIG. 8, microscope sample 21-5).

EXAMPLE 3

Dramatically greater roflumilast crystalline growth was observed in an equimolar N-methyl pyrrolidone:water solution containing roflumilast in excess of drug saturation compared to a 12:4:3 (wt/wt/wt) blend of hexylene glycol: N-methyl pyrrolidone:water (1.2 mole fraction of water) solution having roflumilast added in excess of the solubility limit.

Figure 10:
FIG. 10 shows Sample 21-1 roflumilast crystals suspended in HG:NMP:Water (water mole fraction=1.2) solution after storage for six weeks at room temperature. The roflumilast crystals are 0.02 mm-0.04 mm in length and 0.02 mm in width.

0.0202 grams of roflumilast (Batch A14367P from Interquim S.A.) was mixed with 0.0682 grams of equimolar N-Methyl-2-pyrrolidone:water blend in a liquid scintillation vial. An equimolar blend is 84.5% N-Methyl-2-pyrrolidone (lot SYYN-HJ, TCI) and 15.5% water on a weight/weight percent basis. The 22.85% roflumilast in equimolar N-Methyl-2 pyrrolidone:water was completely dissolved at 25° C. This sample (labeled 13-2) was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 10, microscope sample 20-1).

Figure 11A:
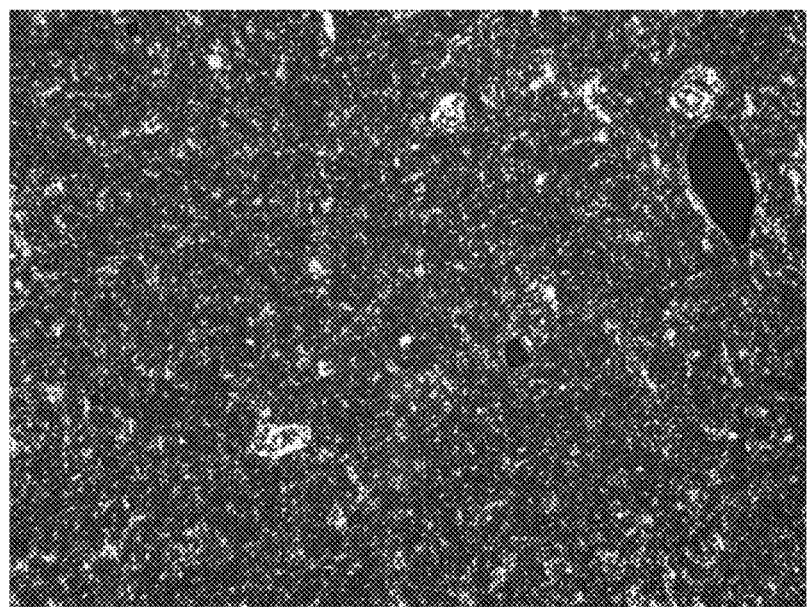
FIGS. 11A and 11B show roflumilast particles precipitated in a cream composition after one freeze thaw cycle.
Figure 11B:
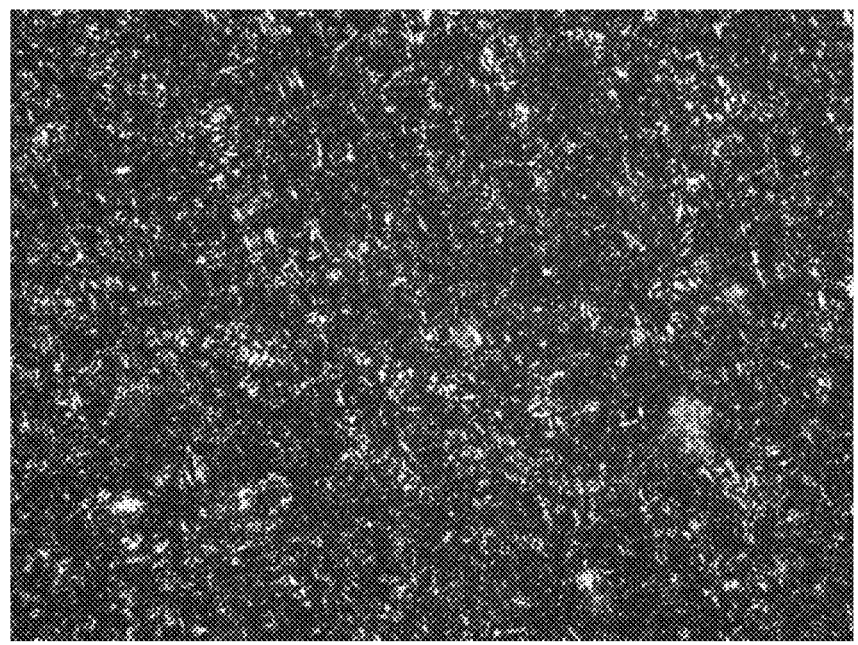

A 0.8152 gram sample of 3.6% roflumilast (Batch A14367P from Interquim S.A.), 60.8% hexylene glycol (lot 1AC0818, Spectrum), 20.0% N-Methyl-2-pyrrolidone (lot SYYN-HJ, TCI) and 15.6% distilled water was mixed on a weight/weight percent basis. This sample (labeled 13-4) was a finely dispersed suspension of roflumilast at 25° C. The sample was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 11, microscope sample 21-1).

EXAMPLE 4

Roflumilast creams were prepared according to the following formulations.

| Formulation 1 (comparative) | |
|---|---|
| Roflumilast | 0.5% w/w |
| White Petrolatum | 10.0% w/w |
| Isopropyl Palmitate | 5.0% w/w |
| Crodafos CES | 10.0% w/w |
| Diethylene glycol monoethyl ether (Transcutol P) | 25% w/w |
| Methylparaben | 0.2% w/w |
| Propylparaben | 0.05% w/w |
| Purified Water | q.s. ad 100 (49.25%) |

| Formulation 2 | |
|---|---|
| Roflumilast | 0.5% w/w |
| White Petrolatum | 10.0% w/w |
| Isopropyl Palmitate | 5.0% w/w |
| Crodafos CES | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.25%) |

After preparation, 0.4222 grams of formulation 1 was sealed in a 1.0 mL CryoTube™ vial and labeled as 36-1. Likewise, 0.3961 grams of formulation 2 was sealed in a 1.0 mL CryoTube™ vial and labeled as 36-2. The two CryoTube™ vials were secured in an envelope end-to-end and placed in the freezer for 17.5 hours. Quickly upon removal from the freezer, a microscopic slide was prepared of each sample and after "thawing" the sample to room temperature (18° C.) a photomicrograph image was captured to characterize differences in precipitated roflumilast crystal growth. See FIGS. 11A and 11B.

EXAMPLE 5

Formulations According to the Invention and of the Prior Art

A formulation of the invention, hereafter referred to as Formulation 3, was made by combining roflumilast with a phosphate ester surfactant and water. The formulation was buffered with NaOH to obtain a pH of 6.5.

A formulation of the invention, hereafter referred to as Formulation 4, was made by combining the above constituents and adding diethylene glycol monoethyl ether. This formulation was buffered with NaOH to obtain a pH of 6.5.

A formulation that is not of the invention, hereafter referred to as Comparative Formulation 5, was made by combining roflumilast with diethylene glycol monoethyl ether. This formulation was gelled with hydroxylpropyl cellulose so that it would have a similar viscosity and spread on the skin like the two phosphate ester surfactant emulsion Formulations 3, and 4. This semisolid formulation was likewise buffered with NaOH to obtain a pH of 6.5.

The compositions of these formulations are shown below in Table 1.

TABLE 1

| | Formulation 3 | Formulation 4 | Comparative Formulation 5 |
|---|---|---|---|
| Roflumilast | 0.15% w/w | 0.15% w/w | 0.15% w/w |
| Crodafos CES cetostearyl alcohol | 10.0% w/w | 10.0% w/w | |

TABLE 1-continued

|  | Formulation 3 | Formulation 4 | Comparative Formulation 5 |
|---|---|---|---|
| dicetyl phosphate |  |  |  |
| ceteth-10 phosphate |  |  |  |
| Diethylene Glycol Monoethyl Ether, NF |  | 25.0% w/w | 25.0% w/w |
| Hydroxypropyl Cellulose |  |  | 0.5% w/w |
| 1N NaOH, NF | q.s. ad pH 6.5 | q.s. ad pH 6.5 | q.s. ad pH 6.5 |
| Purified Water, USP | q.s. ad 100% | q.s. ad 100% | q.s. ad 100% |

EXAMPLE 6—SINGLE DOSE TESTING OF FORMULATIONS OF EXAMPLE 5

Male and female swine (Gottingen Minipig® breed) (Marshall BioResources, North Rose, NY) were ordered to weigh 8 to 12 kg at arrival. On the day prior to administration of one of the topical cream semisolid formulations of Example 5 containing 0.15% roflumilast, the hair was clipped from the back of each animal. The pigs were sedated for the shaving procedure. Care was taken to avoid abrading the skin.

Two (2) grams of one of the cream formulations of Example 5 for each kg of pig weight was distributed over the clipped skin area by gentle inunction with a glass stirring rod or stainless-steel spatula. The cream formulation was applied evenly with a thin, uniform film beginning at the scapular region and moving caudally over the test site. The width of the test site area was bilaterally divided by the spine. Six pigs (3 males and 3 females) were administered a single dose of the Formulation 4. Blood was sampled from the anterior vena cava through the thoracic inlet or other suitable vein pre-dose (time=0) and at 1, 2, 4, 8 and 24 hours post dose administration. A one-week wash out (no product dosed) was sufficient to reduce plasma levels of roflumilast to zero as verified by the pre-dose (time=0) sample. After the washout period, a single dose of formulation 3 was applied. After a second one-week washout period, a single dose of Formulation 5 was applied. Blood samplings were the same for all three groups. The results are shown graphically in FIG. 12.

Figure 12:
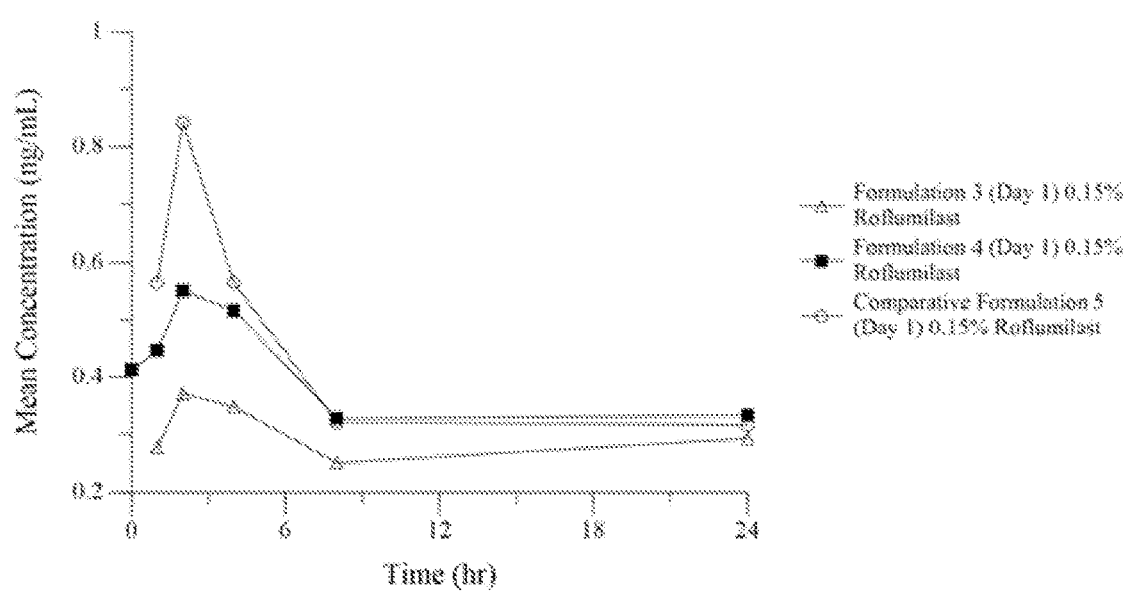
FIG. 12 is a line graph comparing the pharmacokinetic (PK) profile of two formulations of the invention, Formulation 3 and Formulation 4, and a PK profile of a formulation of the prior art, Formulation 5.

As shown in FIG. 12, pigs dosed with Comparative Formulation 5 of the prior art showed a rapid spike to Cmax within 3 hours of dosing. In contrast, pigs dosed with Formulation 3 of the invention containing the phosphate ester surfactant Crodafos CES showed little or no spike to Cmax. Pigs dosed with Formulation 4 of the invention containing both a phosphate ester surfactant and diethylene glycol monoethyl ether, like those dosed with Formulation 3, showed a reduced spike to Cmax as compared to Formulation 5. However, the higher Cmax obtained with Formulation 4 was higher than that for Formulation 3.

The PK data results in the graph of FIG. 12 show that the single dose PK profile data for the formulation containing phosphate ester surfactants lacks a significant spike to Cmax and has a low Cmax of 0.36 ng/mL, while maintaining a mean plasma concentration of 0.34 ng/ml through the 4 hour sample point. This is in contrast to PK data for the DEGEE formulation that rapidly raises to a Cmax of 0.85 ng/ml at 2 hours and then just as quickly drops to 0.57 ng/mL at 4 hours. When the phosphate ester surfactant is added to DEGEE the formulation of the invention, it lacks a significant spike to Cmax and has a low Cmax, while maintaining AUC, in contrast to PK data for the DEGEE formulation which does not contain phosphate ester surfactants. This PK data is especially surprising in view of the fact that the prior art (Bolle) teaches that Cmax and AUC are similar for topical preparations containing roflumilast, irrespective of the composition of the topical formulation. In contrast to what one would expect based on the teachings of the prior art, Formulation 3, containing phosphate ester surfactant, lacks a significant spike to Cmax. Moreover, the mean plasma concentration of 0.34 ng/ml was maintained throughout the 4 hour sample point. In contrast, Formulation 5 containing diethylene glycol monoethyl ether but lacking a phosphate ester surfactant, showed a rapid spike rise to Cmax of 0.85 ng/ml at two hours. When a phosphate ester surfactant was utilized in combination with diethylene glycol monoethyl ether, Formulation 4 administration produced no significant spike to Cmax and had a Cmax between those obtained with Formulations 3 and 5, while maintaining AUC.

EXAMPLE 7—FORMULATION OF THE INVENTION AND A FORMULATION OF THE CLOSEST PRIOR ART

A third embodiment of the invention, hereafter referred to as Formulation 6, was made by combining roflumilast at a concentration of 0.3% w/w with a phosphate ester surfactant and water. The formulation was buffered with NaOH to obtain a pH of 5.5. This formulation is similar to Formulation 3 except that the concentration of roflumilast is 0.3% rather than 0.15% and the emulsion is buffered to a pH value of 5.5 rather than a pH value of 6.5.

A formulation that is not of the invention, hereafter referred to as Comparative Formulation 7, was made by combining roflumilast at a concentration of 0.3% containing a phosphate ester surfactant, a polyoxyl stearyl ether surfactant and diethylene glycol monoethyl ether, as well as other excipients. This formulation is a cream formulation containing a frequently used phosphate ester surfactant that is not Crodafos CES.

A formulation that is not of the invention, hereafter referred to as Comparative Formulation 8, was made by combining roflumilast at a concentration of 0.2%. This formulation is that of the closest prior art known to the inventors and is disclosed in Example 3 of Bolle et al, U.S. Patent Application No. US 2006/0084684.

The compositions of these formulations are shown below in Table 2.

TABLE 2

|  | Formulation 6 | Comparative Formulation 7 | Comparative Formulation 8 |
|---|---|---|---|
| Roflumilast | 0.3% w/w | 0.3% w/w | 0.2% w/w |
| Petrolatum, USP | — | 10.0% w/w | — |
| Isopropyl Palmitate, NF | — | 5.0% w/w | — |
| Medium-Chain Triglycerides | — | — | 25.0% w/w |
| Crodafos CES | 10.0% w/w | — | — |
| cetostearyl alcohol | (6-8% w/w) |  |  |
| dicetyl phosphate | (1-2.5% w/w) |  |  |
| ceteth-10 phosphate | (1-2.5% w/w) |  |  |
| Potassium Cetyl Phosphate |  | 2.0% w/w |  |
| Cetostearyl Alcohol |  | 6.0% w/w | 5.0% w/w |
| Polyoxyl Stearyl Ether |  | 2.0% w/w |  |
| Glyceryl Stearate/ PEG-100 Stearate |  | — | 5.0% w/w |

TABLE 2-continued

|  | Formulation 6 | Comparative Formulation 7 | Comparative Formulation 8 |
|---|---|---|---|
| Diethylene Glycol Monoethyl Ether, NF | — | 25.0% w/w | — |
| Hexylene Glycol, NF | — | 2.0% w/w | — |
| Methylparaben, NF | — | 0.20% w/w | — |
| Propylparaben, NF | — | 0.050% w/w | — |
| 1N NaOH, NF | q.s. ad pH 5.5 | q.s. ad pH 5.5 | — |
| Purified Water, USP | q.s. ad 100% | q.s. ad 100% | q.s. ad 100% |

*The exact ratio of cetostearyl alcohol to dicetyl phosphate to cetheth-10 phosphate in Crodafos CES is consistent between batches of product but is not publicly disclosed by the manufacturer (Croda). The safety data sheet for Crodafos CES states that this emulsifier is composed of 60-80% cetostearyl alcohol, 10-20% dicetyl phosphate and 10-20% cetheth-10 phosphate. To emphasize the similarity in composition between Formulation 5 (phosphate-ester surfactant blend) and Comparative Formulation 6 (phosphate ester and nonionic surfactant blend) and Comparative Formulation 7 (nonionic surfactant blend), the cetostearyl alcohol portion of Crodafos CES is listed separately from the surfactant portion of Crodafos CES in Table 2.

Glyceryl Stearate/PEG-100 Stearate is the nomenclature used by the US Food and Drug Administration to describe the nonionic emulsifier blend sold using the tradename Arlacel® 165 and Tego Care® 150.

Medium-Chain Triglycerides is the nomenclature used by the US Food and Drug Administration to describe the cosmetic ingredient Capryli/Capric Triglyceride which is sold using tradenames including Miglyol® 812 and Crodamole® GTCC.

EXAMPLE 8—14-DAY DOSE TESTING OF FORMULATIONS OF EXAMPLE 7

Male and female swine (Gottingen Minipig® breed) are ordered to weigh 8 to 12 kg at arrival. On the day prior to administration of one of the topical cream semisolid formulations of Example 7, the hair is clipped from the back of each animal. The pigs are sedated for the shaving procedure. Care is taken to avoid abrading the skin.

Two (2) grams of one of the cream formulations of Example 7 for each kg of pig weight is distributed over the clipped skin area by gentle inunction with a glass stirring rod or stainless-steel spatula. The cream formulation is applied evenly with a thin, uniform film beginning at the scapular region and moving caudally over the test site. The width of the test site area is bilaterally divided by the spine. Eighteen pigs are divided into 3 groups of six pigs (3 males and 3 females) and the pigs of each group were dosed with one of the formulations 6, 7, or 8. Blood is sampled from the anterior vena cava through the thoracic inlet or other suitable vein pre-dose (time=0) and at 1, 2, 4, 8 and 24 hours post dose administration. The results are shown graphically in FIG. 13.

Figure 13:
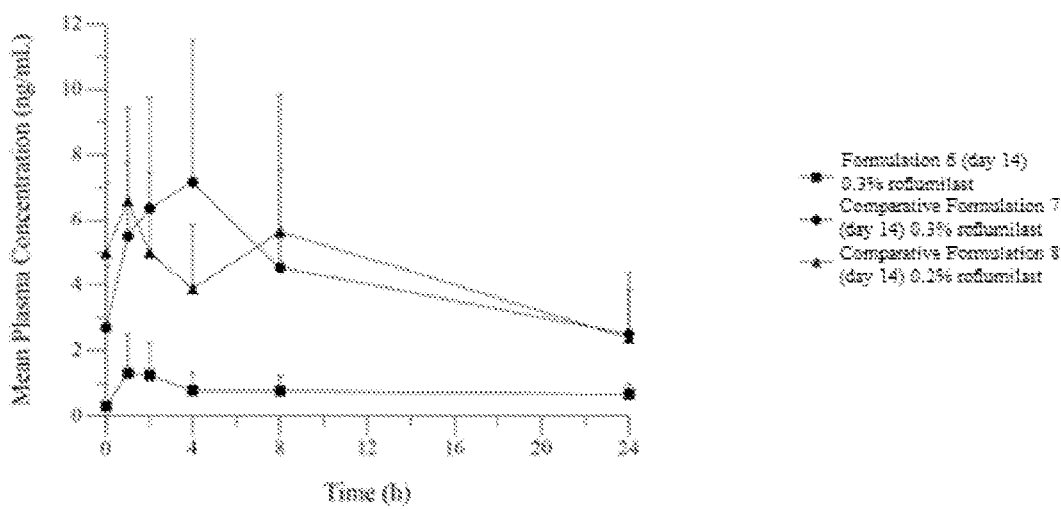
FIG. 13 is a graph comparing the slow rise to Cmax of Formulation 6 (dicetyl phosphate/ceteth-10 phosphate) with the significantly greater roflumilast Cmax peak values (compared to trough T=0 plasma concentrations) following dosing with comparative formulation 7 (potassium cetyl phosphate) and comparative formulation 8 (Cetostearyl Alcohol and Glyceryl Stearate/PEG-100 Stearate).

As shown in FIG. 13, pigs dosed with Formulation 7 of the prior art show a rapid spike to a Cmax value of 6.6 ng/mL at 1 hour after the 14$^{th}$ consecutive daily dose. In contrast, pigs dosed with Formulation 6 of the invention containing the phosphate ester surfactant Crodafos CES show little or no spike to Cmax.

The results show in the graph of FIG. 13, that the steady state PK profile data after 14 days of once daily dosing for the formulation of the invention lacks a significant spike to Cmax and has a low Cmax, while maintaining AUC, in contrast to PK data for the prior art formulation or a formulation using a phosphate ester surfactant that was not Crodafos CES. These results are especially surprising in view of the fact that the prior art (Bolle) teaches that Cmax and AUC are similar for topical preparations containing roflumilast, irrespective of the composition of the topical formulation.

EXAMPLE 9—TESTING FOR MULTIPLE DOSE PHARMACOKINETICS COMPARED TO PRIOR ART

A fourth formulation of the invention is shown in Table 3, hereafter referred to as Formulation 9, was made by combining the above constituents and adding diethylene glycol monoethyl ether, as well as other ingredients to create a complete formulation. This formulation was buffered with NaOH to obtain a pH of 5.5. The qualitative and quantitative composition of Formulation 9 varies only in the amount of roflumilast added to the cream. As a fraction of 1% roflumilast is added, a fraction of 1% of water is removed from the cream.

TABLE 3

| Formulation 9 | |
|---|---|
| Roflumilast | 0.15, 0.3, 0.5 or 1.0% w/w |
| Petrolatum, USP | 10.0% w/w |
| Isopropyl Palmitate, NF | 5.0% w/w |
| Crodafos CES | 10.0% w/w |
| cetostearyl alcohol | (6-8% w/w) |
| dicetyl phosphate | (1-2% w/w) |
| ceteth-10 phosphate | (1-2% w/w) |
| Diethylene Glycol Monoethyl Ether, NF | 25.0% w/w |
| Hexylene Glycol, NF | 2.0% w/w |
| Methylparaben, NF | 0.20% w/w |
| Propylparaben, NF | 0.050% w/w |
| 1N NaOH, NF | q.s. ad pH 5.5 |
| Purified Water, USP | q.s. ad 100% |

Male and female swine (Gottingen Minipig® breed) were ordered to weigh 8 to 12 kg at arrival. On the day prior to administration of a topical cream containing roflumilast, the hair was clipped from the back of each animal. The pigs were sedated for the shaving procedure. Care was taken to avoid abrading the skin.

Figure 14:
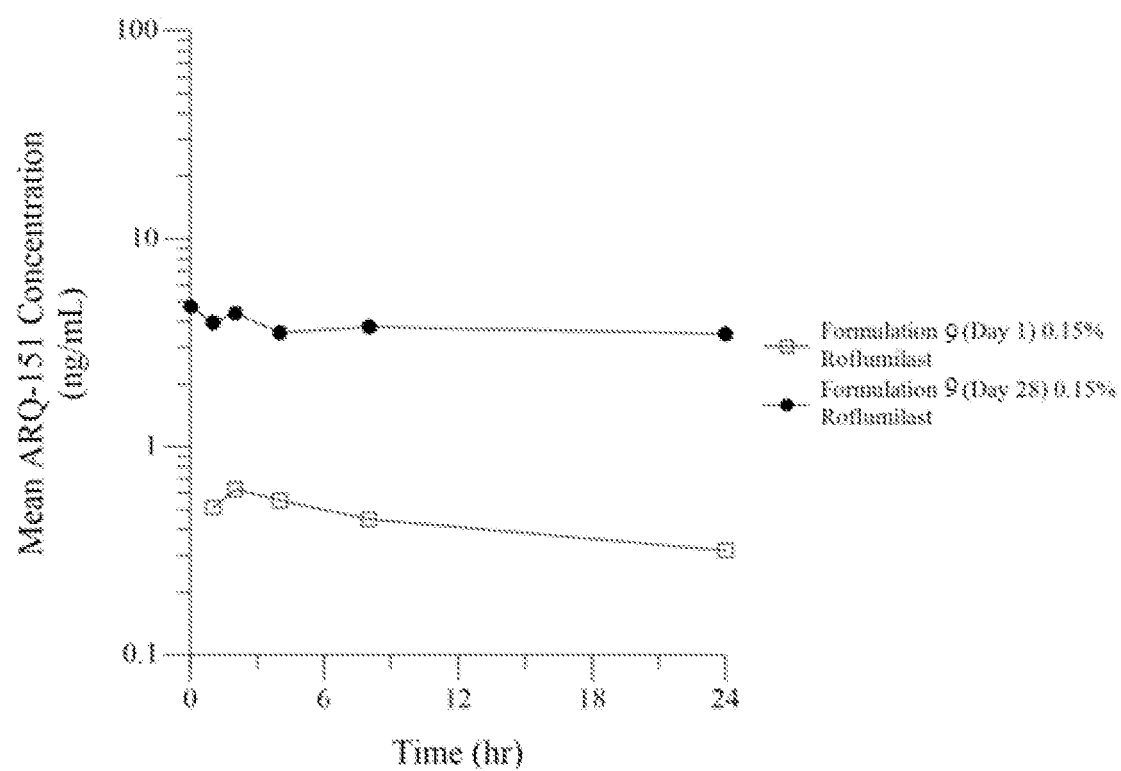
FIG. 14 is a line graph showing Day 1 and Day 28 PK profiles after once daily dosing of 0.15% roflumilast topical cream.
Figure 15:
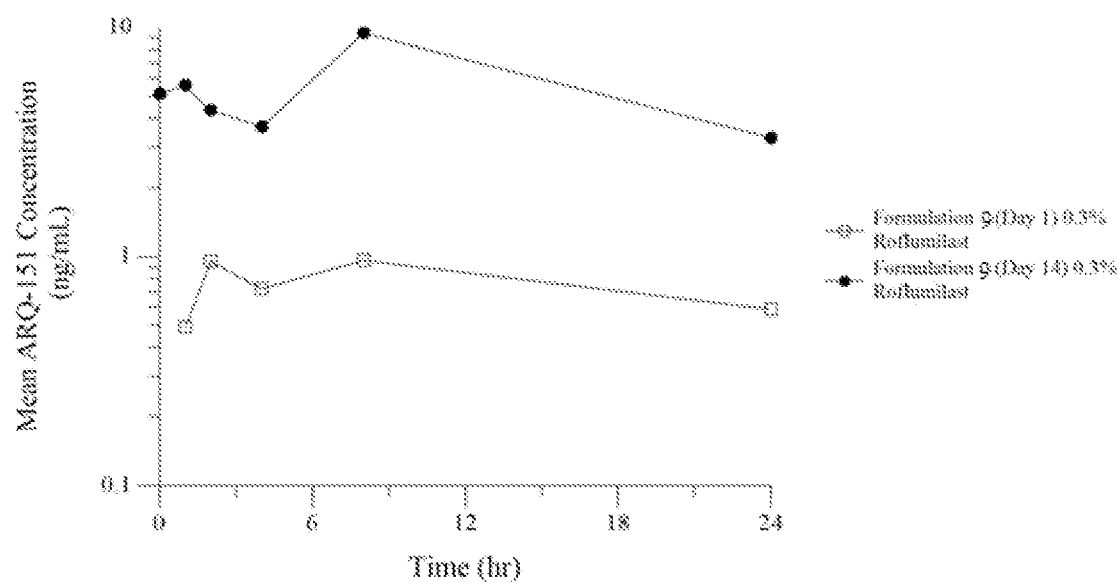
FIG. 15 is a line graph showing Day 1 and Day 14 PK profiles after once daily dosing of 0.3% roflumilast topical cream.
Figure 16:
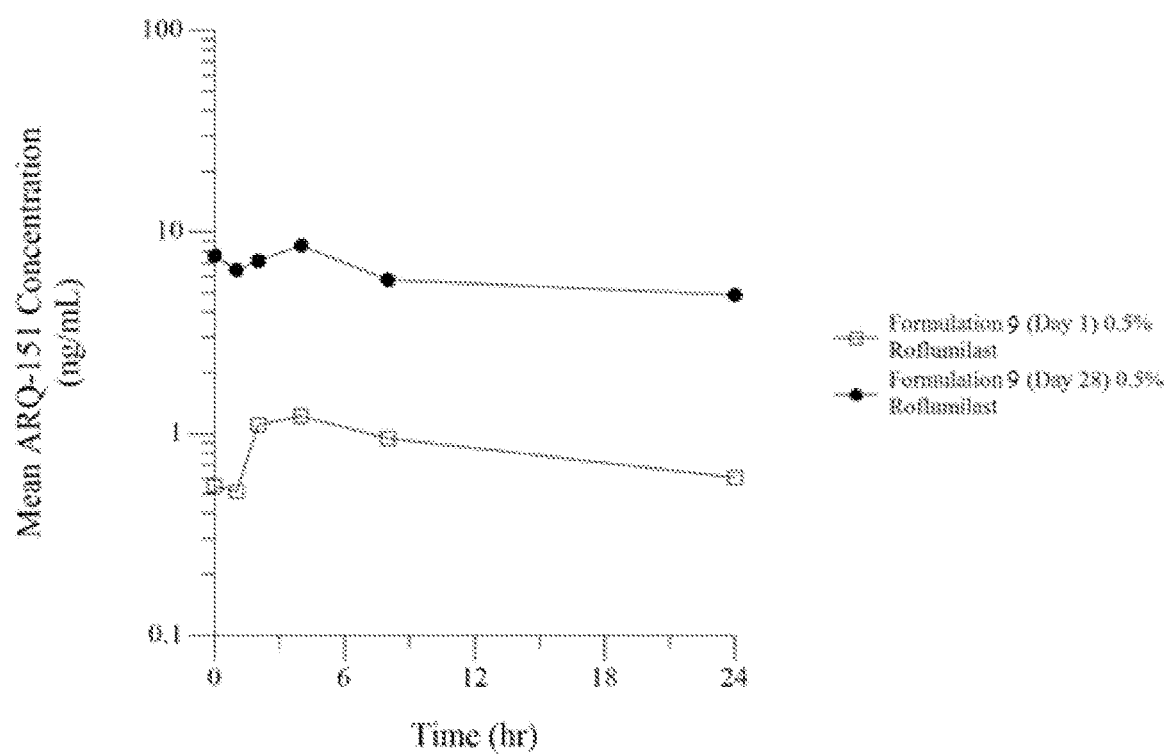
FIG. 16 is a line graph showing Day 1 and Day 28 PK profiles after once daily dosing of 0.5% roflumilast topical cream.
Figure 17:
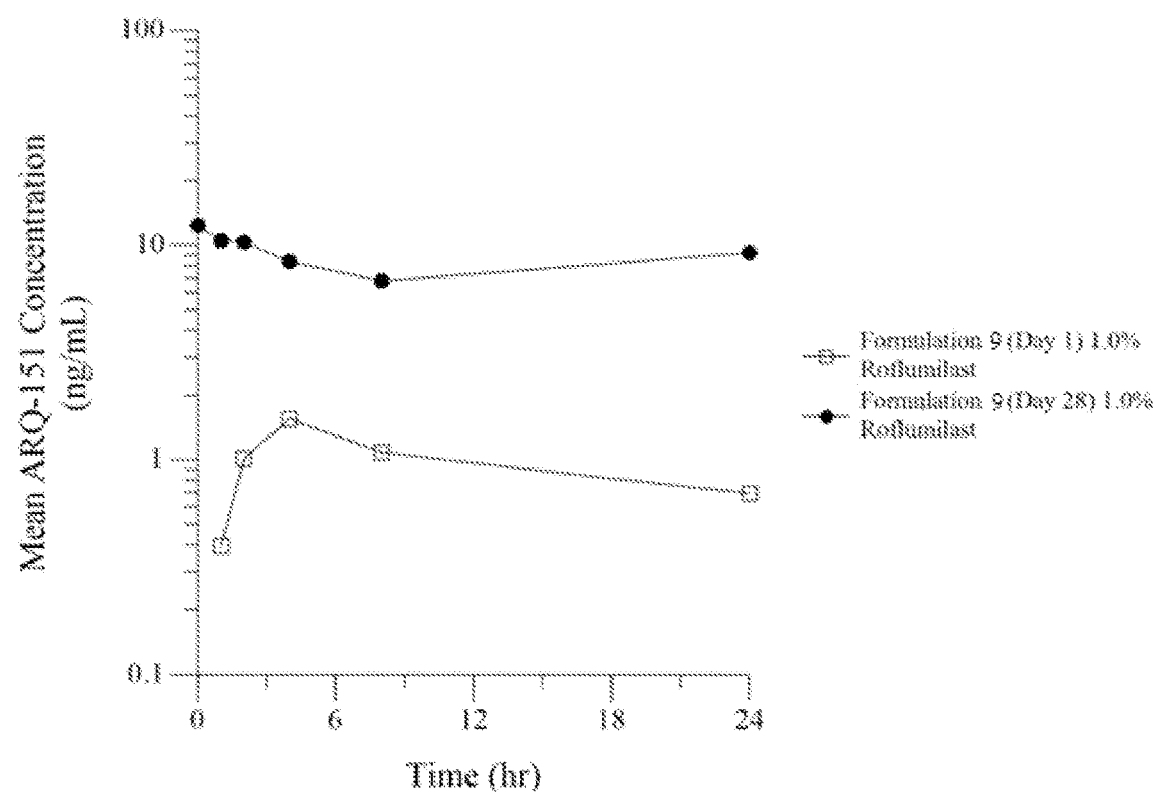
FIG. 17 is a line graph showing Day 1 and Day 28 PK profiles after once daily dosing of 1.0% roflumilast topical cream.

Two (2) grams of the cream Formulation 9 having varying concentrations of roflumilast, for each kg of pig weight was distributed over the clipped skin area by gentle inunction with a glass stirring rod or stainless-steel spatula. The cream was applied evenly with a thin, uniform film beginning at the scapular region and moving caudally over the test site. The width of the test site area was bilaterally divided by the spine. Twenty pigs (10 males and 10 females) were dosed with 1% roflumilast cream, twelve pigs (6 males and 6 females) were dosed with 0.5% roflumilast cream, and twelve pigs (6 males and 6 females) were dosed with 0.15% roflumilast cream, each dosed daily for 28 days. Six pigs (3 males and 3 females) were each dosed daily with 0.3% roflumilast cream (formulation 9) for 14-days. Blood was sampled from a suitable vein pre-dose (time=0), and at times 1, 2, 4, 8 and 24 hours post dose administration on day 1 and day 28 (or day 14 for 0.3% roflumilast) of dosing. The results are shown graphically in FIG. 14 (0.15% roflumilast cream), in FIG. 15 (0.3% roflumilast), in FIG. 16 (0.5% roflumilast cream), and in FIG. 17 (1.0% roflumilast cream) and in tabular form in Table 4.

As shown in each of FIGS. 14 to 17, the gradual ascent to Cmax is evident from the day 1 pharmacokinetic profile. What is most striking and surprising about the data shown in FIGS. 14 to 17 is the very flat and prolonged plateau in blood levels of the drug following Cmax in the day 28 or day 14 (0.3% roflumilast cream) pharmacokinetic profile, after reaching steady state drug delivery.

TABLE 4

| Topical Product Dosed | Trough (T = 0) (ng/ml) | Peak or Cmax (ng/ml) |
|---|---|---|
| 0.15% Roflumilast Cream (FIG. 14-Steady State Day 28) | 4.5 (females) 5.0 (males) | 4.9 (females) 5.0 (males) |
| 0.3% Roflumilast Cream (FIG. 15-Steady State Day 14) | 3.7 (females) 6.6 (males) | 4.5 (females) 6.6 (males) |
| 0.5% Roflumilast Cream (FIG. 16-Steady State Day 28) | 8.5 (females) 6.7 (males) | 10.7 (females) 8.2 (males) |
| 1% Roflumilast Cream (FIG. 17-Steady State Day 28) | 16.3 (females) 8.4 (males) | 16.3 (females) 10.0 (males) |

Likewise, the data of Table 4 show an extremely small variation in blood concentration between the trough and peak (Cmax) following the attainment of steady state for each of the four concentrations of roflumilast when the formulation of the present invention is topically applied.

EXAMPLE 10—CLINICAL STUDY IN SUBJECTS WITH PLAQUE PSORIASIS

Study Design

ARQ-151 is a topical cream which contains roflumilast. This phase 1/2a clinical trial enrolled two cohorts: Cohort 1 evaluated a single administration of ARQ-151 cream 0.5% and Cohort 2 evaluated ARQ-151 cream 0.5% or 0.15% applied once daily for 28 days. In Cohort 1, subjects applied ARQ-151 cream 0.5% to 25 cm$^2$ of psoriatic plaque(s). Subjects were screened (Visit 1), returned to the clinic for treatment (Visit 2) and PK blood draws, had a follow-up visit at 24 hours after the baseline visit for a PK blood draw (Visit 3), and received a follow-up telephone contact for safety evaluation 7 days after Visit 3. Subjects enrolled in Cohort 1 could be enrolled in Cohort 2 if they met eligibility criteria; subjects from Cohort 1 who rolled into Cohort 2 had all of their plaque(s) treated in Cohort 2 up to 5% body surface area (BSA).

Cohort 2 used a parallel-group, double-blind, vehicle-controlled study design. Subjects were randomly assigned in a 1:1:1 ratio to ARQ-151 cream 0.5%, ARQ-151 cream 0.15%, or a matched vehicle, which was applied to all psoriatic plaques (except on the face, intertriginous areas, scalp, palms, and soles) up to an application area of 5% BSA. Subjects in Cohort 2 had screening and baseline visits, follow-up visits at weeks 1, 2, 3, and 4, an additional visit at day 29 for a final pharmacokinetic sample collection, and a follow-up telephone call for safety evaluation at week 5.

Cohort 1 received open-label treatment, without assignment or blinding. Assignment to treatment arm in Cohort 2 was performed using a computer-generated randomization list. Randomization was generated using SAS by an unblinded Premier Research statistician who was otherwise not involved in study conduct. The block size was 3; 72 total blocks were used. Everyone was blinded to treatment.

This study was conducted in accordance with the principles of the Declaration of Helsinki and Good Clinical Practice. The protocol was approved by Research Review Board, Inc., Richmond Hill, ON, Canada for all sites. All subjects provided written informed consent prior to initiation of any study-specific procedures. This trial was registered under ClinicalTrials.gov #NCT03392168.

Manufacture of ARQ-151 Cream (Formulation 9)

A target amount of 480 grams sterile water for irrigation-USP was accurately weighed into a 1000 ml glass beaker and 20 grams of sodium hydroxide pellets-NF was added and mixed using a stir bar until complete dissolution. This solution was set aside and labeled 1 N Sodium Hydroxide.

Target weights pf 1,000 grams white petrolatum-USP, 500 grams isopropyl palmitate-NF, and 1,000 grams of phosphate-ester self-emulsifying wax (CRODAFOS™ CES) were weighed into a 4 L glass beaker and heated on a hot plate to 75° C. to 80° C. while mixing with a propeller mixer. The mixture was labeled Oil Phase and was maintained at 75° C. to 80° C.

To the Main Manufacturing Vessel (a 20 L stainless steel vessel) a target weight of 4,225 grams of sterile water for irrigation-USP and a target weight 300 grams 1N sodium hydroxide were added and heated on a hot plate to 75° C. to 80° C. This was recorded as the Aqueous Phase and was maintained at 75° C. to 80° C.

Target weights of 2,400 grams of Transcutol P-NF, 200 grams of hexylene glycol-NF, 20.0 grams of methylparaben-NF, and 5.0 grams of propylparaben NF were accurately weighed into a 7 L stainless steel beaker and propeller mixed until a clear homogeneous solution was obtained. Sufficient potency corrected roflumilast was added to this solution to obtain either a 0.15% roflumilast cream or a 0.5% roflumilast cream and this was labeled the API Phase.

The Oil Phase that was maintained at 75° C. to 80° C. was slowly added to the Aqueous Phase maintained at 75° C. to 80° C. in the Main Manufacturing Vessel with homogenizer mixing until a smooth, homogeneous cream was obtained. Using propeller mixing, the cream was cooled to 45° C. to 50° C. The API Phase was slowly added to the cream in the main manufacturing vessel and was mixed with the homogenizer. The pH of the finished cream was measured and adjusted to within the pH range of 5.1 to 5.9 using 1 N Sodium Hydroxide or Diluted Hydrochloric Acid, 10% (w/v)-NF. After bulk product release, the cream was filled into aluminum ¾×3¾ #16 sealed white tubes and the tubes crimped to provide the primary container closure system.

Patients

To be eligible for enrollment in Cohort 1, subjects had to be ≥18 years of age with ≥25 cm$^2$ of chronic plaque psoriasis. To be eligible for enrollment in Cohort 2, subjects also had to have chronic plaque psoriasis of ≥6 months duration covering 0.5% to 5.0% of total BSA excluding the face, scalp, intertriginous areas, palms, and soles. Subjects needed to have at least 1 (and up to 3) target plaque(s)≥9 cm$^2$ in size with a Target Plaque Severity Score (TPSS)≥4. Target plaques could be located anywhere on the body (excluding the face, scalp, intertriginous areas, palms, and soles), including the knees and elbows. Key exclusion criteria included: non-plaque forms of psoriasis, drug-induced psoriasis, skin conditions that would interfere with study assessments, known allergies to excipients in ARQ-151 cream, hypersensitivity to PDE-4 inhibitors, inability to discontinue use of strong P-450 cytochrome inducers or P-450 cytochrome inhibitors, inability to refrain from use of a tanning bed, inability to discontinue systemic or topical therapies for the treatment of psoriasis, active infection requiring oral or intravenous antibiotics, antifungal, or antiviral agents within 7 days of baseline, or current or history of cancer within 5 years except for fully excised skin basal cell carcinoma, cutaneous squamous cell carcinoma, or cervical carcinoma.

Treatments and Application

Formulation 9, also known as ARQ-151 cream, contained 0.5% or 0.15% roflumilast. Vehicle contained all ingredients in the ARQ-151 cream except roflumilast. In Cohort 1, ARQ-151 cream 0.5% was applied in the clinic to 25 $cm^2$ of psoriatic plaque(s). In Cohort 2, all psoriatic lesions up to 5% BSA (except for those on the face, scalp, intertriginous areas, palms, and soles) were treated at home by subjects once daily for 4 weeks. Subjects were instructed by study staff on proper dosing and administration of ARQ-151 cream and vehicle.

Study Assessments

Assessments of efficacy (Cohort 2 only), pharmacokinetics (both cohorts), and safety (both cohorts) were conducted. The primary and secondary efficacy endpoints were calculated based on the product of Target Plaque Severity Score (TPSS) and Target Plaque Area (TPA). The TPSS was determined for each target plaque on each subject as the sum of erythema, thickness, and scaling scores, each rated on a scale of 0 (none) to 4 (very severe) and was identical to the severity scoring used in the PASI. TPA ($cm^2$) was determined by multiplying the longest diameter (cm) of the target plaque by the widest perpendicular diameter (cm). Thus, the product of TPSS×TPA was roughly analogous to a PASI for the treated plaque. TPSS and TPA assessments were conducted at screening, baseline, and weeks 1, 2, 3, and 4.

Pharmacokinetic profiles for roflumilast and its active metabolite roflumilast N-oxide12 were determined from plasma. Blood samples for pharmacokinetic analyses were collected on day 1 at 1, 2, 4, and 6 hours after ARQ-151 application. On day 28, samples were collected before dosing (trough level) and at 1, 2, 4, 6, and 24 hours after application.

Safety endpoints included the type and incidence of treatment-emergent adverse events (TEAEs) and serious adverse events (SAEs); application site reactions; and changes in physical examinations, vital signs, electrocardiograms, and clinical laboratory parameters. Safety was assessed at all study visits and at telephone follow-up. Skin irritation was assessed on days 1 and 2 for Cohort 1 and at baseline and visits 3 (week 1), 4 (week 2), 5 (week 3), and 6 (week 4) for Cohort 2. Skin irritation was evaluated using a scale developed by Berger and Bowman ranging from 0 (no evidence of irritation) to 7 (strong reaction spreading beyond application site). Additionally, other clinical signs of irritation were scored on an 'A' (slight glazed appearance) to 'F' (small petechial erosions and/or scabs) scale. An additional safety endpoint was the results from the Depressive Symptomatology Questionnaire, 14 which was administered at screening, week 2, and week 4. The questionnaire is a 16-item inventory of depressive symptoms, with each item scored on a range of 0 to 3. Depression severity is based on score category, where total score≤5 represents no depression; 6-10 represents mild depression; 11-15 represents moderate depression; 16-20 represents severe depression; and ≥21 represents very severe depression.

Statistical Considerations

For Cohort 2, a sample size of 24 subjects per arm (72 total subjects) was estimated to provide 80% power to detect a difference of 23% in the mean percentage change from baseline in the primary endpoint between the ARQ-151 cream and matching vehicle arm. This estimation was based on a 1-way analysis of variance at the $\alpha=0.025$ significance level. To accommodate a 16% drop-out rate, the total sample size was increased to 84 subjects.

TEAEs were coded using the Medical Dictionary for Regulatory Activities (MedDRA) version 20.1, and severity was graded on a 5-point scale of Grade 1 (mild), Grade 2 (moderate), Grade 3 (severe), Grade 4 (life-threatening consequences), or Grade 5 (death related to AE).

Pharmacokinetic parameters were calculated using the plasma concentration values of roflumilast and roflumilast N-oxide (ng/mL) at each nominal time point with Phoenix WinNonlin (v8.0) using standard noncompartmental analysis. The area under the concentration time curve (AUC) was estimated using the linear trapezoidal interpolation method. The maximum plasma concentration (Cmax) and time to reach maximum concentration (Tmax) were based on direct assessment. Sample concentration values reported to be below the limit of quantification (BLQ; <0.100 ng/mL) were ignored.

The primary efficacy endpoint was the difference in mean percentage change from baseline at week 4 in the product of TPSS×TPA between each dose of ARQ-151 cream and vehicle control. The primary efficacy endpoint was analyzed using a mixed model for repeated measures with center within country, treatment, study visit, and treatment-by-study-visit interaction as fixed effects and baseline TPSS×TPA score as a covariate. Mean differences between visit value and baseline were calculated for each treatment. Mean percentage change from baseline for each ARQ-151 dose and corresponding vehicle were compared using an unstructured covariance structure unless the model did not converge; in that case the appropriate covariance structure was investigated. The Bonferroni method was used to control for multiplicity, where the significance level for each of pairwise comparisons of active vs placebo was at $\alpha=0.025$.

Secondary efficacy endpoints included the difference in mean percentage change from baseline at weeks 1, 2, and 3 in composite TPSS×TPA score, TPSS, and TPA between each dose of ARQ-151 cream and vehicle control. Statistical analyses of secondary efficacy endpoints were the same as those used for the primary endpoint, except no adjustments for multiplicity were used and all analyses were conducted at the $\alpha=0.05$ level.

In a post hoc analysis, the percentage of subjects with 75% and 90% improvement from baseline in TPSS×TPA (75% responders and 90% responders) at each study visit through week 4 were also evaluated.

Safety analyses were conducted with the safety population, which comprised all subjects who received at least 1 dose of study drug and were based on treatment received. Pharmacokinetic analyses were conducted with the pharmacokinetic population, which included all subjects who consented for sampling and received active drug with sufficient plasma concentrations of roflumilast to define a profile. Efficacy analyses were conducted with the modified intent-to-treat population, which was composed of all subjects in Cohort 2 who received ≥1 dose of study drug and had ≥1 post-baseline efficacy evaluation.

No imputation was used for missing data. Data processing, tabulation of descriptive statistics, calculation of inferential statistics, and graphical representations (except for PK parameter estimation) were performed primarily using SAS (release 9.4). All PK parameter estimations were performed using WinNonlin® version 6.4 or later.

Results

Patients

Subjects were recruited from 7 study sites in Canada and from 1 site in the US between Dec. 5, 2017 (first patient enrolled) and May 2, 2018 (last follow-up visit). Eight subjects enrolled in Cohort 1, and 89 subjects enrolled in Cohort 2, including subjects randomly assigned to ARQ-151 cream 0.5% (N=30), ARQ-151 cream 0.15% (N=28), and vehicle (N=31). All subjects in Cohort 1 received treatment and completed the study, and 6 also participated in Cohort 2. Four subjects in Cohort 2 discontinued early from the study because of loss to follow-up (n=3) or other reasons (n=1). There were no discontinuations due to AEs. The safety populations comprised all 8 subjects in Cohort 1 and all 89 subjects in Cohort 2. The PK population included 20 subjects who received Formulation 9 (ARQ-151 cream) 0.5% and 22 subjects who received Formulation 9 (ARQ-151 cream) 0.15%. The efficacy population comprised all subjects in Cohort 2.

The mean age (standard deviation [SD]) was 51.6 (16.9) years for Cohort 1 and mean age ranged from 47.5 to 55.3 years across Cohort 2 treatment arms (Table 5). Most subjects were white. The average BSA of involvement was ~2% in all treatment groups. Of the 89 subjects enrolled in Cohort 2, 35 (39.3%) had target plaques located on the knees, elbows, or both.

TABLE 5

Subject Characteristics (Safety Population)

| | Cohort 1 | Cohort 2 | | |
|---|---|---|---|---|
| | ARQ-151 0.5% (N = 8) | ARQ-151 0.5% (N = 30) | ARQ-151 0.15% (N = 28) | Vehicle (N = 31) |
| Age, mean years (SD) | 51.6 (16.9) | 49.9 (15.9) | 55.3 (13.2) | 47.5 (14.7) |
| Sex, n (%) | | | | |
| Male | 1 (12.5) | 16 (53.3) | 19 (67.9) | 18 (58.1) |
| Female | 7 (87.5) | 14 (46.7) | 9 (32.1) | 13 (41.9) |
| Race, n (%) | | | | |
| White | 8 (100) | 25 (83.3) | 24 (85.7) | 22 (71.0) |
| Asian | 0 | 2 (6.7) | 2 (7.1) | 8 (25.8) |
| Black/African American | 0 | 2 (6.7) | 2 (7.1) | 0 |
| Other | 0 | 1 (3.3) | 0 | 1 (3.2) |
| Psoriasis-affected BSA, mean $m^2$ (SD) | NC | 3.06 (1.39) | 2.73 (1.32) | 2.21 (1.05) |

BSA, body surface area;
NC, not collected;
SD, standard deviation.

Efficacy Results

Figure 18A:
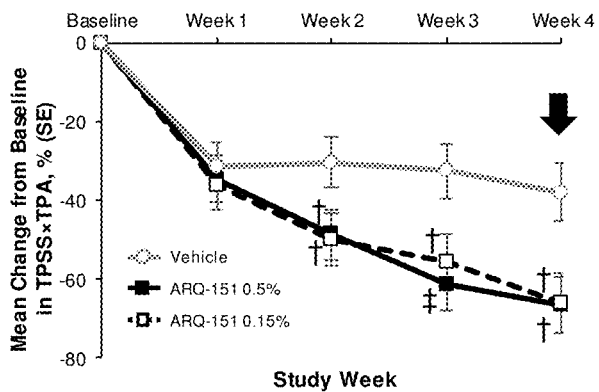
FIGS. 18A, 18B and 18C show changes in baseline in Target Plaque Severity Score and/or Target Plaque Area for 0.15% roflumilast topical cream and 0.5% roflumilast topical cream.

The primary efficacy endpoint was met: the mean percentage change from baseline in TPSS×TPA at week 4 was significantly different from vehicle for ARQ-151 cream 0.5% (P=0.0007) and ARQ-151 cream 0.15% (P=0.0011) (FIG. 18A). For both concentrations of ARQ-151 cream, 66%-67% improvement from baseline was observed in the primary endpoint after 4 weeks of treatment vs 38% for vehicle, based on least square (LS) mean percentage change from baseline. Statistical separation from vehicle was reached for both drug product concentrations as early as week 2 of treatment, and the difference between drug product and vehicle continued to increase through week 4. Both ARQ-151 cream 0.5% and 0.15% showed similar efficacy in this primary endpoint throughout the study duration.

Figure 18B:
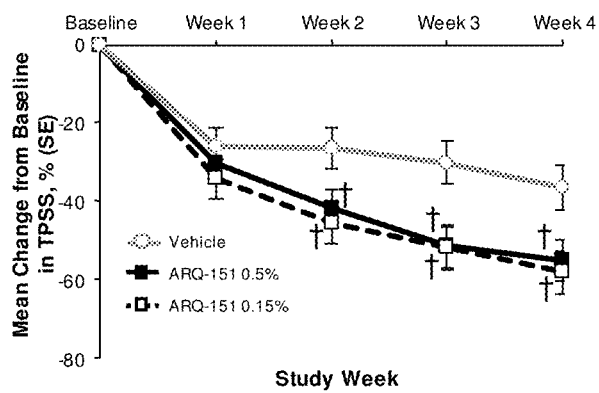
Figure 18C:
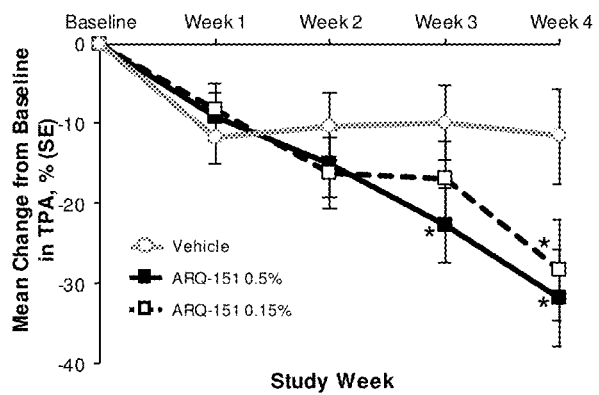

Secondary efficacy endpoints of change from baseline in TPSS (FIG. 18B) and change from baseline in TPA (FIG. 18C) were statistically significantly different between ARQ-151 at both active concentrations and vehicle after 4 weeks of treatment. For both active concentrations of ARQ-151 vs vehicle, change from baseline in TPSS, but not TPA, reached statistical significance as early as 2 weeks.

Patients receiving ARQ-151 cream 0.5%, 0.15% and vehicle after 4 weeks of treatment were compared to baseline, along with their respective TPSS×TPA scores. Of note, the vehicle-treated subjects seemed to have improvement mainly in the appearance of scaling (predictable for an emollient cream). Both subjects receiving ARQ-151 cream 0.5% and 0.15% show examples of substantial improvement in the elbows or knees, which can be treatment-resistant areas of psoriasis. Indeed, 39.3% of subjects had target plaques on the elbows and/or knees.

In a post hoc analysis, 75% responder rates (75% improvement from baseline in TPSS×TPA) at week 4 were also evaluated. In the ARQ-151 cream 0.5% group, 10 subjects (35.7%) achieved this level of improvement (P=0.0090), and in the ARQ-151 cream 0.15% group, 7 subjects (25.9%) were 75% responders (P=0.0700). There were two 75% responders (6.4%) in the vehicle group. In this same analysis, 90% responder rates at week 4 were also evaluated. In the ARQ-151 cream 0.5% group, 4 subjects (14.3%) achieved this level of improvement, and in the ARQ-151 cream 0.15% group, 3 subjects (11.1%) were 90% responders; however, none of the 90% responder rates was statistically significant. There was one 90% responder (3.2%) in the vehicle group.

Pharmacokinetic Results

In Cohort 1, limited evidence of systemic plasma exposure to roflumilast or roflumilast N-oxide was observed after a single topical administration of ARQ-151 0.5% to 25 cm2 of psoriatic plaques (data not shown). In Cohort 2, systemic plasma exposure to roflumilast and roflumilast N-oxide was observed following single or multiple applications of Formulation 9 (ARQ-151) to psoriatic plaques covering 0.5% to 5% BSA (Table 8, FIG. 19A for 0.5% Formulation 9, ARQ-151 cream and FIG. 19B for 0.15% Formulation 9, ARQ-151 cream). On day 1, roflumilast but not roflumilast N-oxide exposure appeared to increase in a dose-dependent manner. At day 28, the plasma concentration vs time profiles were relatively flat (very small peak to trough differences) suggesting that roflumilast and roflumilast N-oxide exposure achieved steady state and appeared to increase in a dose-dependent manner. The ratio of N-oxide to roflumilast after topical administration ranged from 4.7 to 5.9, compared with 12 after oral administration of roflumilast, the latter being higher due to increased contribution from first pass metabolism.

Figure 19A:
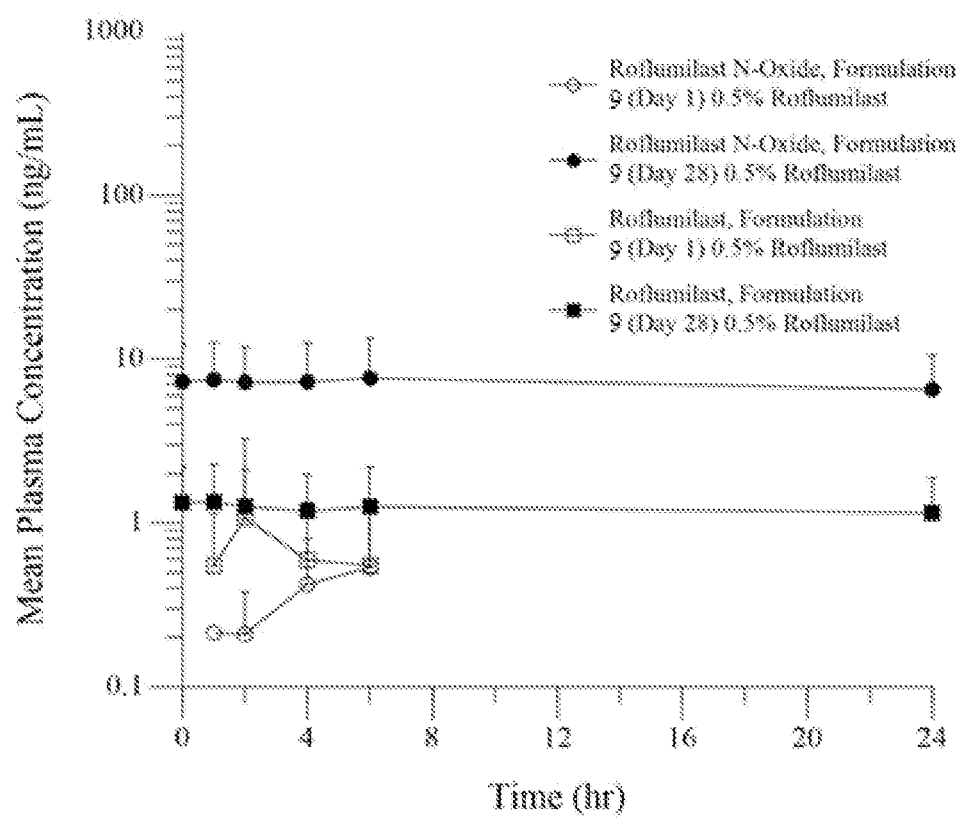
FIGS. 19A and 19B show roflumilast and roflumilast N-oxide plasma concentrations at day 1 and day 28 (pharmacokinetic population) for 0.15% roflumilast topical cream and 0.5% roflumilast topical cream.
Figure 19B:
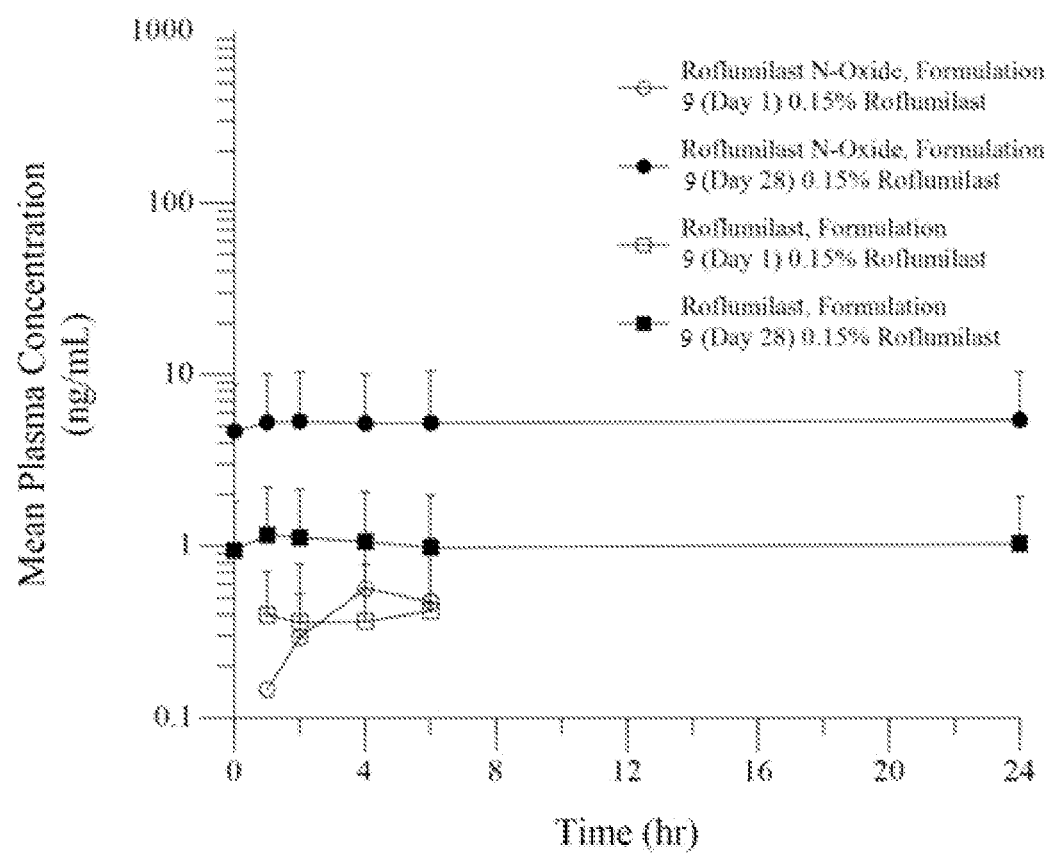
Figure 20A:
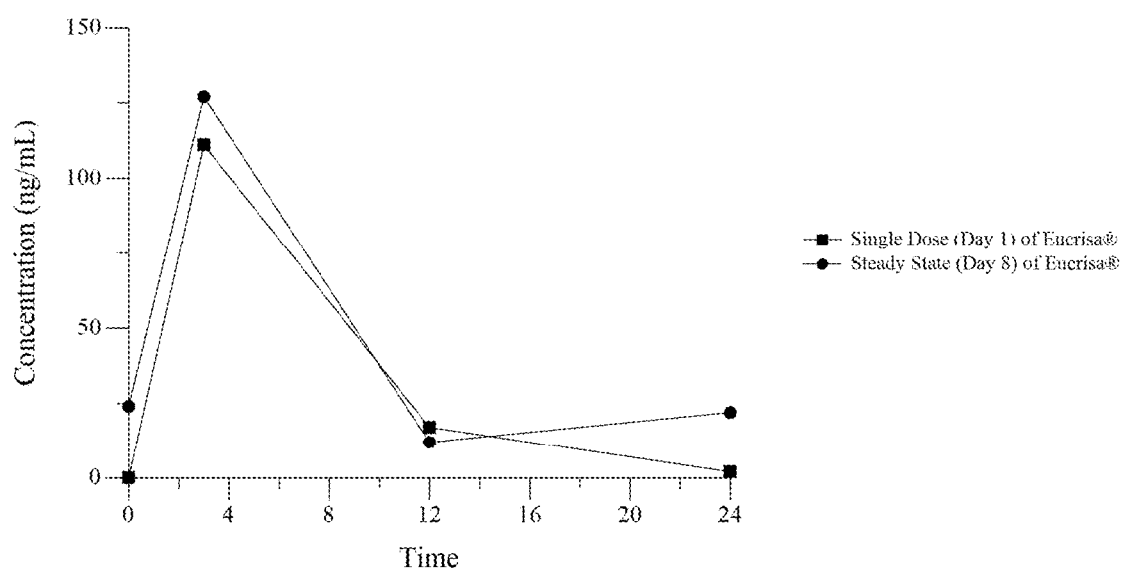
FIGS. 20A and 20B are line graphs showing day 1 and day 8 PK profiles after once daily dosing of Crodafos-CES creams containing either 0.3% crisaborole or 0.3% roflumilast.
Figure 20B:
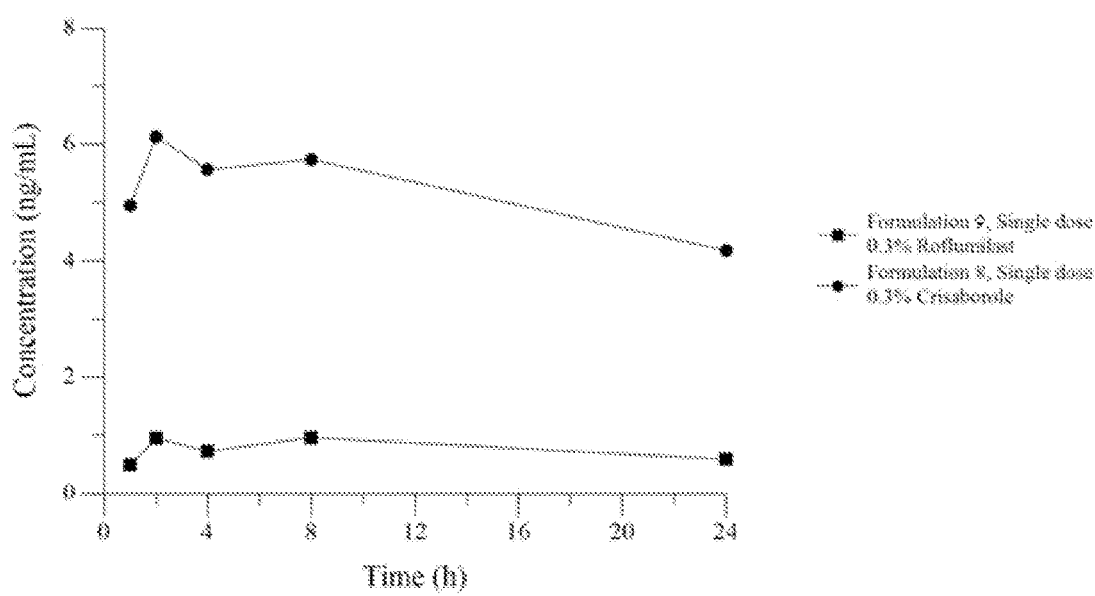
Figure 21:
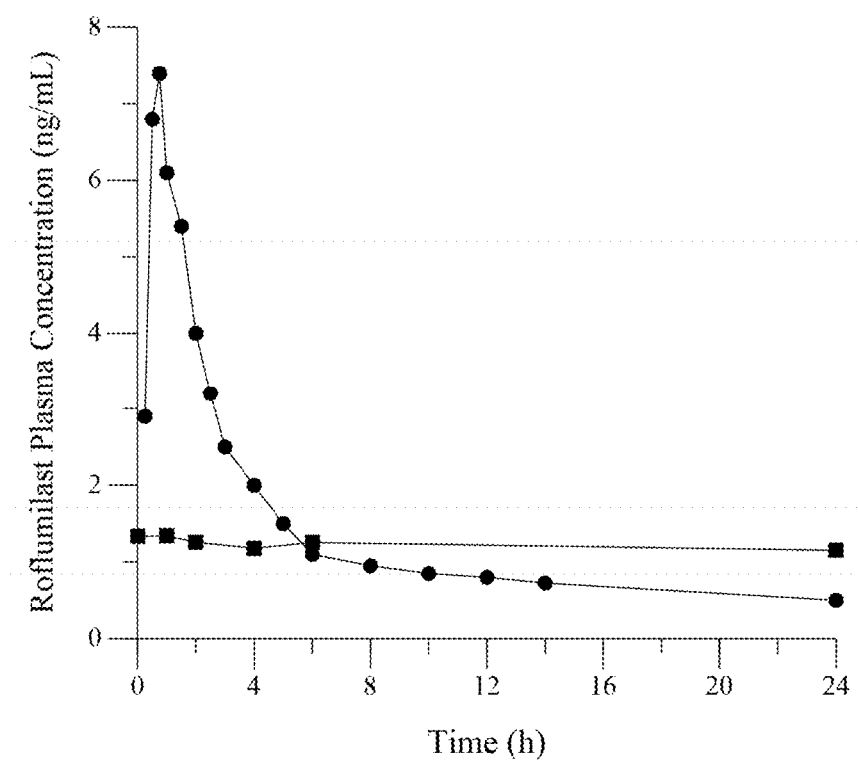
FIG. 21 is a line graph comparing roflumilast plasma concentration over time after 500 mcg once daily oral roflumilast (closed circles) and topical 0.5% ARQ-151 cream (closed squares) 0-24 hours on day 28 of once a day dosing. The oral roflumilast data (closed circles) was extracted from a plot in the publication T. D Bethke and G. Lahu, 2011, Int J of Clin Pharm and Ther, 49(1):51-57. [n=20 subjects; Time=0 (day 28 pre-dose blood draw) 1.33 ng/mL; Time=1.0 hour 1.34 ng/mL; Time=2.0 hour 1.26 ng/mL; Time=4.0 hour 1.18 ng/mL; Time=6.0 hour 1.25 ng/mL; Time=24.0 hour 1.15 ng/mL].

As shown in FIGS. 19A and 19B, when roflumilast is formulated in a cream containing the phosphate ester surfactant Crodafos CES, the gradual ascent to Cmax is evident in the single dose and steady-state pharmacokinetic profile. As shown in FIGS. 19A and 19B, there is a very flat and prolonged plateau in blood levels of the drug following Cmax for the 24-hours following the first application of 0.15% or 0.5% Formulation 9 (ARQ-151 cream) in human subjects. The pharmacokinetic profile of roflumilast after dosing the skin with Formulation 9 has the same low rise to Cmax shape when applied to humans or pigs.

TABLE 6

Pharmacokinetic Parameters (Pharmacokinetic Population; Cohort 2)

| | ARQ-151 0.5% | ARQ-151 0.15% |
|---|---|---|
| Day 1 | | |
| Roflumilast | | |
| $AUC_{0-last}$, mean h × ng/mL (SD) [n] | 4.37 (5.84) [10] | 2.34 (2.56) [7] |
| $C_{max}$, mean ng/mL (SD) [n] | 1.38 (2.26) [10] | 0.578 (0.468) [7] |
| $T_{max}$, mean h {minimum, maximum} [n] | 3.20 {1.00, 6.00} [10] | 3.71 {1.00, 6.00} [7] |
| Roflumilast N-oxide | | |
| $AUC_{0-last}$, mean h × ng/ml (SD) [n] | 2.61 (2.13) [4] | 3.18 (2.54) [2] |
| $C_{max}$, mean ng/ml (SD) [n] | 0.965 (0.858) [4] | 1.07 (0.950) [2] |
| $T_{max}$, mean h [minimum, maximum] [n] | 6.00 {6.00, 6.00} [4] | 6.00 {6.00, 6.00} [2] |
| Day 28 | | |
| Roflumilast | | |
| $AUC_{0-last}$, mean h × ng/ml (SD) [n] | 29.2 (19.9) [20] | 24.4 (22.8) [21] |
| $C_{max}$, mean ng/ml (SD) [n] | 1.48 (0.978) [20] | 1.30 (1.06) [21] |
| $T_{max}$, mean h [minimum, maximum] [n] | 3.70 {0.00, 24.0} [20] | 4.95 {0.00, 24.0} [21] |
| Roflumilast N-oxide | | |
| $AUC_{0-last}$, mean h × ng/ml (SD) [n] | 172 (116) [20] | 127 (119) [22] |
| $C_{max}$, mean ng/mL (SD) [n] | 8.41 (5.54) [20] | 6.11 (5.53) [22] |
| $T_{max}$, mean h [minimum, maximum] [n] | 8.25 {0.00, 24.0} [20] | 8.59 {0.00, 24.0} [22] |

$AUC_{0-last}$, area under the concentration time curve until the last measurable time point;

$C_{max}$, maximum plasma concentration;

$T_{max}$, time to maximum plasma concentration.

Safety Results

In Cohort 1, only 1 subject reported a TEAE, which was considered unrelated to treatment (Table 7). In Cohort 2, the percent of TEAEs in the 0.15% group was lower than in the 0.5% or vehicle groups (7.1% vs 23.3% and 25.8%, respectively, for treatment-related TEAEs; and 25% vs 40% and 35.5%, respectively, for all TEAEs) (Table 7); all were mild or moderate in severity. No SAE was reported in this study, and no subject discontinued from the study because of a TEAE. All treatment-related TEAEs were associated with the application site, accounting for 17 events. Application site TEAEs were generally mild in severity and number (16 events were mild and 1 event was moderate) and showed no consistent differences between drug product and vehicle. No changes in physical examinations, vital signs, electrocardiograms, or clinical laboratory parameters were considered clinically meaningful. There were no clinically significant differences in weight changes between treatment groups. One subject in the 0.5% treatment group reported a single episode of nausea of moderate severity, but no further episodes in the remaining 3 weeks of the study. No subjects reported vomiting or diarrhea. No signs of skin irritation (dermal reactions) were noted in Cohort 1. For Cohort 2, mean (SD) dermal reaction scores at baseline for ARQ-151 cream 0.5%, 0.15%, and vehicle were 0.2 (0.5), 0.0 (0.2), and 0.2 (0.4), respectively, and at week 4 were 0.1 (0.5), 0.0 (0.0), and 0.1 (0.4).

TABLE 7

Summary of Safety (Safety Population)

| | Cohort 1 | Cohort 2 | | |
|---|---|---|---|---|
| | ARQ-151 0.5% (N = 8) | ARQ-151 0.5% (N = 30) | ARQ-151 0.15% (N = 28) | Vehicle (N = 31) |
| Subjects with, n (%): | | | | |
| ≥1 TEAE | 1 (12.5) | 12 (40.0) | 7 (25.0) | 11 (35.5) |
| Treatment-related TEAE | 0 | 7 (23.3) | 2 (7.1) | 8 (25.8) |
| TEAE leading to discontinuation | 0 | 0 | 0 | 0 |
| SAE | 0 | 0 | 0 | 0 |
| Maximum severity of TEAEs, n (%) | | | | |
| Mild | 0 | 7 (23.3) | 3 (10.7) | 6 (19.4) |
| Moderate | 1 (12.5) | 5 (16.7) | 4 (14.3) | 5 (16.1) |
| Application site TEAEs, n (%) | | | | |
| Erythema | 0 | 4 (13.3) | 1 (3.6) | 4 (12.9) |
| Pain | 0 | 2 (6.7) | 1 (3.6) | 5 (16.1) |
| Edema | 0 | 1 (3.3) | 0 | 1 (3.2) |
| Papules | 0 | 1 (3.3) | 0 | 1 (3.2) |
| Pruritus | 0 | 1 (3.3) | 1 (3.6) | 0 |

SAE, serious adverse event;

TEAE, treatment-emergent adverse event.

Discussion

In this phase 1/2a clinical trial, Formulation 9 (ARQ-151 cream) 0.5% and 0.15% was well tolerated, safe, and effective for the treatment of chronic plaque psoriasis. Formulation 9 (ARQ-151 cream) at both doses tested demonstrated strong efficacy as shown by statistically significant reductions in plaque severity and size compared to vehicle.

Statistically significant efficacy of ARQ-151 (Formulation 9 containing 0.15% or 0.5% roflumilast) as compared to vehicle in the primary study endpoint was observed with both active doses as early as 2 weeks after initiation of treatment, and differences between ARQ-151 and vehicle continued to increase through the last visit at 4 weeks. LS mean TPSS×TPA values decreased 38% with vehicle over the course of the study; the preponderance of this effect occurred during week 1 of treatment, which was likely contributed to by apparently decreased scaling to the observer's eye caused by the emollient cream. There was no difference in efficacy between ARQ-151 cream 0.5% and 0.15% in the primary endpoint (percentage change from baseline in TPSS×TPA) at week 4. However, the 75% responder rates at week 4 suggested the 0.5% cream was somewhat more efficacious (35.7%; P=0.0090 vs vehicle) than the 0.15% concentration (25.9%; P=0.0700). With both active drug concentrations after 4 weeks of dosing, TPSS×TPA values were already reduced by 66%-67% from baseline based on LS means. However, TPSS×TPA did not plateau in subjects treated with ARQ-151, suggesting that a longer duration of treatment might provide even greater efficacy. The TPSS×TPA endpoint was chosen to be analogous to whole-body Psoriasis Area and Severity Index (PASI) measurements. Both use the same plaque severity scale, which was applied to 1-3 target lesions in the current study vs the entire body with PASI. The TPA 'area' function is different from the area of plaque involvement assessment in PASI, but we would propose that the product of TPSS×TPA provides an analogous assessment of 'target plaque(s)' to PASI for the entire body. Based on this assumption, the efficacy of topical ARQ-151 after 4 weeks of dosing (with 35.7% of subjects reaching 75% improvement for the 0.5% cream) may be comparable to that of the class 1 steroid betamethasone dipropionate 0.064% (32.7% PASI 75 response rate after 4 weeks of dosing) in the phase 3 studies of Taclonex®.

The safety profile of Formulation 9 (ARQ-151 cream) at both 0.5% and 0.15% was similar to vehicle, which is explained, at least in part, by the pharmacokinetic findings. When administered orally for COPD, roflumilast may be associated with gastrointestinal side effects (diarrhea, nausea, vomiting), psychiatric disturbances (insomnia, anxiety, depression, suicidal thoughts or other mood changes), weight loss in a minority of patients, and headache. Typically, clinical development of PDE-4 inhibitors for oral use has been limited by gastrointestinal effects such as nausea and vomiting. Indeed, nausea, vomiting, psychiatric disturbances, and weight loss are believed to be mediated at the level of the brain. In contrast to oral administration, topical administration of roflumilast in our study was associated with a slow ascent to maximum plasma concentrations over multiple days, and a flat exposure to roflumilast and its active metabolite roflumilast N-oxide throughout the dosing period (i.e. $C_{max} \sim C_{min}$ across dosing interval). The lack of nausea and vomiting seen in the present study could possibly be attributed the lack of 'peak to trough' $C_{max}$ variation; lower $C_{max}$ values than observed following oral administration; or bypassing of the gastrointestinal tract with topical administration. The absence of psychiatric disturbances and weight loss seen in our studies may also be explained by the markedly different PK of topical vs oral administration. PDE-4 inhibition represents a validated mechanism of action for oral psoriasis therapy (Otezla), but a new mechanism of action for topical psoriasis therapy. Patients with mild to moderate disease represent the majority of the psoriasis population. This patient population has not benefited from the recent introduction of biologic therapies, which are used in patients with more severe disease. However, it is not surprising that roflumilast is an effective modality for the treatment of psoriasis. Roflumilast is a highly potent PDE-4 inhibitor, exhibiting half maximal inhibitory concentration ($IC_{50}$) values of both roflumilast and roflumilast N-oxide for the different PDE-4 isoforms and subtypes at subnanomolar potency. Rolumilast is 50- to 300-fold more potent than either apremilast or crisaborole against the different PDE-4 isoforms and subtypes. The oral dose of roflumilast, at only 0.5 mg per day, is reflective of this extremely high potency.

Further modifications, uses, and applications of the invention described herein will be apparent to those skilled in the art. It is intended that such modifications be encompassed in the following claims.

EXAMPLE 11—PREPARING A FOAM FORMULATION

A fifth formulation of the invention is shown in Table 8, hereinafter referred to as Formulation 10. Formulation 10 is a foam concentrate which can be mixed with a propellant to produce a foam. Sixty four grams of the foam concentrate was blended with 8-10 grams of AP-70 propellant to make a foam.

TABLE 8

| Formulation 10 | |
| --- | --- |
| Roflumilast | 0.15, 0.3, 0.5 or 1.0% w/w |
| Petrolatum, USP | 5.0% w/w |
| Isopropyl Palmitate, NF | 2.5% w/w |
| Crodafos CES | 2% w/w |
| cetostearyl alcohol | (1.2-1.6% w/w) |
| dicetyl phosphate | (0.2-0.5% w/w) |
| ceteth-10 phosphate | (0.2-0.5% w/w) |
| Diethylene Glycol Monoethyl Ether, NF | 25.0% w/w |
| Hexylene Glycol, NF | 2.0% w/w |
| Methylparaben, NF | 0.20% w/w |
| Propylparaben, NF | 0.050% w/w |
| 1N NaOH, NF | q.s. ad pH 5.5 |
| Purified Water, USP | q.s. ad 100% |

EXAMPLE 12—COMPARISON OF ADVERSE EVENT PROFILES OF DALIRESP AND TOPICAL FORMULATIONS

Treatment of 4,438 patients with once daily DALIRESP® 500 mcg tablets was associated with an increase in psychiatric adverse reactions and weight loss. In 8 controlled clinical trials 5.9% (263) of patients treated with DALIRESP® 500 mcg daily reported psychiatric adverse reactions compared to 3.3% (137) treated with placebo. The most commonly reported psychiatric adverse reactions were insomnia, anxiety, and depression which were reported at higher rates in those treated with DALIRESP® 500 mcg daily (2.4%, 1.4%, and 1.2% for DALIRESP® versus 1.0%, 0.9%, and 0.9% for placebo, respectively). Instances of suicidal ideation and behavior, including completed suicide, have been observed in clinical trials. Three patients experienced suicide-related adverse reactions (one completed suicide and two suicide attempts) while receiving DALIRESP® compared to one patient (suicidal ideation) who received placebo. Cases of suicidal ideation and behavior, including completed suicide, have been observed in the post-marketing setting in patients with or without a history of depression. Weight loss was a common adverse reaction in DALIRESP® clinical trials and was reported in 7.5% (331) of patients treated with DALIRESP® 500 mcg once daily compared to 2.1% (89) treated with placebo [see DALIRESP® 500 mcg package insert Adverse Reactions (6.1)]. In addition to being reported as adverse reactions, weight was prospectively assessed in two placebo-controlled clinical trials of one-year duration. In these studies, 20% of patients receiving roflumilast experienced moderate weight loss (defined as between 5-10% of body weight) compared to 7% of patients who received placebo. In addition, 7% of patients who received roflumilast compared to 2% of patients receiving placebo experienced severe (>10% body weight) weight loss. During follow-up after treatment discontinuation, the majority of patients with weight loss regained some of the weight they had lost while receiving DALIRESP®. (Section 5.2 and 5.3 of the Daliresp package insert)

In contrast to the psychiatric adverse reactions and weight loss associated with orally administered roflumilast (Daliresp® 500 µg tablets), no significant safety concerns or signals have been identified during the completed or ongoing clinical studies of roflumilast cream or roflumilast foam. It is estimated that about 2,412 clinical trial subjects have been exposed to at least one dose of topical roflumilast cream or roflumilast foam. While adverse events associated with marketed oral roflumilast (Daliresp® 500 µg tablets), such as depression, weight loss and gastrointestinal adverse events, were assessed with regard to topical roflumilast cream and roflumilast foam studies, the side effects associated with oral administration of roflumilast have not been observed in roflumilast cream and roflumilast foam clinical studies. The pharmacokinetic profile of topical roflumilast appears to be distinct from that of oral roflumilast likely due to the lack of 'peak to trough' Cmax variation, lower Cmax values than observed following oral administration, and/or bypassing of the gastrointestinal tract with topical administration.

The invention claimed is:

1. A topical roflumilast pharmaceutical composition comprising:
   (i) roflumilast in an amount of 0.05-1.0% w/w;
   (ii) water;
   (iii) a hydrophobic component;
   (iv) a solvent comprising diethylene glycol monoethyl ether; and
   (v) a surfactant;
   wherein said topical roflumilast composition is an emulsion, and
   wherein said topical roflumilast composition has a roflumilast absorption profile that produces in a patient following administration, a plasma concentration time curve having a delayed Tmax relative to oral administration of roflumilast.

2. The composition of claim 1, wherein the surfactant comprises a blend of ceteraryl alcohol, dicetyl phosphate, and ceteth-10 phosphate.

3. The composition of claim 1, wherein the hydrophobic component comprises petrolatum.

4. The composition of claim 2, wherein the hydrophobic component comprises petrolatum.

5. The composition of claim 1, wherein said Tmax is between about 3 and 9 hours at steady state.

6. The composition of claim 2, wherein said Tmax is between about 3 and 9 hours at steady state.

7. The composition of claim 3, wherein said Tmax is between about 3 and 9 hours at steady state.

8. The composition of claim 4, wherein said Tmax is between about 3 and 9 hours at steady state.

9. The composition of claim 5, wherein said Tmax is between about 8 and 9 hours at steady state.

10. The composition of claim 6, wherein said Tmax is between about 8 and 9 hour at steady state.

11. The composition of claim 7, wherein said Tmax is between about 8 and 9 hours at steady state.

12. The composition of claim 8, wherein said Tmax is between about 8 and 9 hours at steady state.

* * * * *